United States Patent
Son et al.

(10) Patent No.: US 9,419,224 B2
(45) Date of Patent: Aug. 16, 2016

(54) FLUORO GROUP-CONTAINING COMPOUND, FLUORO GROUP-CONTAINING POLYMER, ORGANIC LIGHT EMITTING DEVICE INCLUDING THE POLYMER, AND METHOD OF MANUFACTURING THE DEVICE

(75) Inventors: Jhun-mo Son, Yongin-si (KR); Won-jae Joo, Yongin-si (KR); Ho-suk Kang, Yongin-si (KR); Hye-yeon Yang, Yongin-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 604 days.

(21) Appl. No.: 12/823,832

(22) Filed: Jun. 25, 2010

(65) Prior Publication Data

US 2011/0121338 A1 May 26, 2011

(30) Foreign Application Priority Data

Nov. 20, 2009 (KR) .................. 10-2009-0112812

(51) Int. Cl.
*H01L 51/54* (2006.01)
*C07C 43/225* (2006.01)
*C08G 65/00* (2006.01)
*H01L 51/00* (2006.01)
*C09K 11/06* (2006.01)
(Continued)

(52) U.S. Cl.
CPC .......... *H01L 51/0039* (2013.01); *C07C 43/225* (2013.01); *C07D 265/38* (2013.01); *C08G 61/122* (2013.01); *C09K 11/06* (2013.01); *H01L 51/0043* (2013.01); *C07C 2103/18* (2013.01); *C07C 2103/94* (2013.01); *C08G 2261/146* (2013.01); *C08G 2261/148* (2013.01); *C08G 2261/3142* (2013.01); *C08G 2261/3245* (2013.01); *C08G 2261/412* (2013.01); *C08G 2261/95* (2013.01); *H01L 51/5012* (2013.01); *H01L 51/5052* (2013.01)

(58) Field of Classification Search
CPC ............ C07C 2103/18; C07C 2103/94; C07C 43/225; C07D 265/38; C08G 2261/146; C08G 2261/148; C08G 2261/3142; C08G 2261/3245; C08G 2261/412; C08G 2261/95; C08G 61/122; H01L 51/0039; H01L 51/0043; H01L 51/5012; H01L 51/5052; H01L 51/54; C09K 11/06; H05B 33/14
See application file for complete search history.

(56) References Cited

U.S. PATENT DOCUMENTS 5,250,667 A   10/1993   Lau et al.
6,905,787 B2 *  6/2005   Ise ................. 428/690
(Continued)

FOREIGN PATENT DOCUMENTS

| CN | 1621431 A | 6/2005 |
| JP | 2003277305 A | 10/2003 |
| KR | 2008111968 A * | 12/2008 |

OTHER PUBLICATIONS

European Journal of Organic Chemistry, (2007), (31), pp. 5244-5249.*

(Continued)

*Primary Examiner* — Dawn Garrett
(74) *Attorney, Agent, or Firm* — Cantor Colburn LLP

(57) ABSTRACT

A fluoro group-containing compound, a fluoro group-containing polymer, an organic light emitting device including the polymer, and a method of manufacturing the organic light emitting device are provided.

12 Claims, 3 Drawing Sheets

(51) Int. Cl.
*C07D 265/38* (2006.01)
*C08G 61/12* (2006.01)
*H01L 51/50* (2006.01)

(56) References Cited

U.S. PATENT DOCUMENTS

| | | | |
|---|---|---|---|
| 7,524,567 B2* | 4/2009 | Park et al. | 428/690 |
| 7,939,622 B2* | 5/2011 | Park et al. | 528/424 |
| 2002/0173617 A1* | 11/2002 | Yasuda et al. | 528/422 |
| 2004/0056266 A1* | 3/2004 | Suh et al. | 257/99 |
| 2004/0137273 A1* | 7/2004 | Tak et al. | 428/690 |
| 2004/0260047 A1* | 12/2004 | Chen et al. | 528/4 |
| 2005/0048313 A1* | 3/2005 | Sotoyama | 428/690 |
| 2005/0186446 A1* | 8/2005 | Shitagaki et al. | 428/690 |
| 2005/0244674 A1* | 11/2005 | Yasuda et al. | 428/690 |
| 2007/0213503 A1* | 9/2007 | Sasaki et al. | 528/394 |
| 2007/0292716 A1* | 12/2007 | Shiobara et al. | 428/690 |
| 2008/0113468 A1* | 5/2008 | Spreitzer et al. | 438/99 |
| 2009/0167170 A1* | 7/2009 | Burroughes et al. | 313/504 |
| 2010/0133992 A1* | 6/2010 | Yang et al. | 313/504 |
| 2010/0240856 A1* | 9/2010 | Veinot et al. | 528/86 |
| 2011/0175069 A1* | 7/2011 | Son et al. | 257/40 |
| 2012/0217445 A1* | 8/2012 | Fukushima et al. | 252/500 |

OTHER PUBLICATIONS

Neilson et al., "Synthesis and properties of perfluorocyclobutyl (PFCB) polymers for light emission", Polymer Preprints (American Chemical Society, Division of Polymer Chemistry), (2005), 46(2), pp. 653-654.*
Abstract for CN 101575508 A (publication date Nov. 11, 2009).*
Macromolecules, (2010), 43(8), pp. 3613-3623.*
Journal of Polymer Science, Part A: Polymer Chemistry, (2007), 45(9), pp. 1746-1757.*
Korean Office Action Dated Oct. 8, 2015, of the Korean Patent Application No. 10-2009-0112812 with English Translation.
Xianshun Zeng et al. "Functionalized 8 nm Long Aryleneethynylene Molecular Wire with Alkyne Termini" Eur J. Org. Chem. 2007, 5244-5249.

* cited by examiner

FLUORO GROUP-CONTAINING COMPOUND, FLUORO GROUP-CONTAINING POLYMER, ORGANIC LIGHT EMITTING DEVICE INCLUDING THE POLYMER, AND METHOD OF MANUFACTURING THE DEVICE

CROSS-REFERENCE TO RELATED APPLICATIONS

This application claims priority to Korean Patent Application No. 10-2009-0112812, filed on Nov. 20, 2009, and all the benefits accruing therefrom under 35 U.S.C. §119, the content of which in its entirety is herein incorporated by reference.

BACKGROUND

1. Field

The present disclosure relates to a compound, a polymer, an organic light emitting device including the polymer, and a method of manufacturing the organic light emitting device.

2. Description of the Related Art

Organic light-emitting devices include a pair of electrodes and an organic layer interposed between the electrodes, such that when a current is supplied to the electrodes, electrons and holes injected from the electrodes are re-combined in the organic layer, thereby emitting light. Accordingly, organic light emitting devices are self-emission-type devices. Organic light emitting devices are lightweight, and can be easily manufactured using a relatively small number of components. In addition, organic light emitting devices provide high-quality images and have wide viewing angles. Furthermore, organic light emitting devices provide high color purity, accurately realize mobile images, have low power consumption, and are operated at low voltage. Due to these characteristics, organic light emitting devices are suitable for mobile electronic devices.

A typical organic light emitting device has a structure including a substrate and an anode, a hole transport layer ("HTL"), an emissive layer ("EML"), an electron transport layer ("ETL"), and a cathode which are sequentially stacked on the substrate.

When a current is supplied to the anode and the cathode, holes injected from the anode move to the EML via the HTL, and electrons injected from the cathode move to the EML via the ETL. The holes and electrons recombine in the EML to generate excitons. The excitons radioactively decay to emit light having a wavelength corresponding to a band gap of the molecule.

Materials that are used in organic layers may be classified as vacuum depositable materials or solution coatable materials, according to the method for preparing the organic layer. The solution coatable materials are miscible with a solvent to form a composition that may be coated on a substrate. The composition may be applied to the substrate using inkjet printing, screen printing, spin coating, and the like.

SUMMARY

One embodiment of this disclosure provides a fluoro group-containing compound.

Further embodiments of this disclosure provide a polymer, an organic light emitting device including the polymer, and a method of manufacturing the organic light emitting device.

According to one embodiment, there is provided a fluoro group-containing compound represented by Formula 1 below:

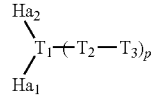

Formula 1 wherein $Ha_1$ and $Ha_2$ are each independently —F, —Cl, or —Br;

$T_1$ is a substituted or unsubstituted $C_6$-$C_{30}$ aromatic group or a substituted or unsubstituted $C_3$-$C_{30}$ heteroaromatic group;

$T_2$ is a bivalent linking group represented by —[C($R_1$)($R_2$)]$_q$—, wherein $R_1$ and $R_2$ are each independently selected from a hydrogen atom, a halogen atom, a hydroxyl group, an amino group, a cyano group, a carboxylic acid group, a substituted or unsubstituted $C_1$-$C_{30}$ alkyl group, and a substituted or unsubstituted $C_2$-$C_{30}$ alkenyl group, q is an integer ranging from 1 to about 20, and optionally at least one —C($R_1$)($R_2$)— may be replaced by a group independently selected from —O—, —C(=O)—, —S—, a substituted or unsubstituted $C_6$-$C_{30}$ arylene group, and a substituted or unsubstituted $C_3$-$C_{30}$ heteroarylene group;

$T_3$ is represented by —($R_3$)$_r$—$R_4$, wherein $R_3$ is selected from a fluoro group-containing $C_1$-$C_{30}$ alkylene group, a fluoro group-containing $C_2$-$C_{30}$ alkenylene group, a fluoro group-containing $C_6$-$C_{30}$ arylene group, and a fluoro group-containing $C_3$-$C_{30}$ heteroarylene group, $R_4$ is selected from a hydrogen atom, a halogen atom, a hydroxyl group, an amino group, a cyano group, and a carboxylic acid group, and r is an integer ranging from 1 to about 10, wherein each $R_3$ may be same or different from any other $R_3$; and p is an integer ranging from 1 to about 5.

According to another aspect of the present invention, there is provided a fluoro group-containing polymer represented by Formula 11 below:

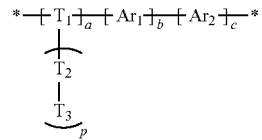

Formula 11 wherein $T_1$ is a substituted or unsubstituted $C_6$-$C_{30}$ aromatic ring or a substituted or unsubstituted $C_3$-$C_{30}$ heteroaromatic group;

$T_2$ is a bivalent linking group represented by —[C($R_1$)($R_2$)]$_q$—, wherein $R_1$ and $R_2$ are each independently selected from a hydrogen atom, a halogen atom, a hydroxyl group, an amino group, a cyano group, a carboxylic acid group, a substituted or unsubstituted $C_1$-$C_{30}$ alkyl group, and a substituted or unsubstituted $C_2$-$C_{30}$ alkenyl group, q is an integer ranging from 1 to about 20, and optionally at least one —C($R_1$)($R_2$)— may be replaced by a group independently selected from —O—, —C(=O)—, —S—, a substituted or unsubstituted $C_6$-$C_{30}$ arylene group, and a substituted or unsubstituted $C_3$-$C_{30}$ heteroarylene group;

$T_3$ is represented by —($R_3$)$_r$—$R_4$, wherein $R_3$ is selected from a fluoro group-containing $C_1$-$C_{30}$ alkylene group, a fluoro group-containing $C_2$-$C_{30}$ alkenylene group, a fluoro group-containing $C_6$-$C_{30}$ arylene group, and a fluoro group-containing $C_3$-$C_{30}$ heteroarylene group, $R_4$ is selected from a hydrogen atom, a halogen atom, a hydroxyl group, an amino group, a cyano group, and a carboxylic acid group, and r is an integer ranging from 1 to about 10, wherein each $R_3$ may be same or different from each other;

p is an integer ranging from 1 to 5;

$Ar_1$ and $Ar_2$ are each independently selected from a substituted or unsubstituted $C_6$-$C_{30}$ arylene group; a substituted or unsubstituted $C_3$-$C_{30}$ heteroarylene group; and a system including at least two groups independently selected from substituted or unsubstituted $C_6$-$C_{30}$ arylene groups and substituted or unsubstituted $C_3$-$C_{30}$ heteroarylene groups, which two groups are connected to each other by a single bond or by a linking group represented by —N($R_{11}$)—, wherein $R_{11}$ is a hydrogen atom, a substituted or unsubstituted $C_1$-$C_{30}$ alkyl group, or a substituted or unsubstituted $C_6$-$C_{30}$ aryl group; and a, b, and c are each independently a real number satisfying $0<a\leq0.99$, $0<b\leq0.99$, and $0\leq c\leq0.99$, and $a+b+c=1$.

According to another embodiment, an organic light emitting device comprises a substrate; a first electrode; a second electrode; an intermediate layer that is interposed between the first electrode and the second electrode and comprising a fluoro group-containing polymer as described above; and an emission layer ("EML") that is formed close to the intermediate layer.

According to another embodiment, a method of manufacturing an organic light emitting device comprises forming a first electrode on a substrate;

forming an intermediate layer comprising a fluoro group-containing polymer as described above by applying a first composition for forming an intermediate layer, wherein the composition comprises the fluoro group-containing polymer as described above and a first solvent, to the first electrode, and baking the first composition at a temperature for a time period suitable for removing the first solvent;

forming an emission layer by applying a second composition for forming an emission layer including an emission layer-forming material and a second solvent to the intermediate layer, and heat-treating the second composition; and forming a second electrode on the emission layer.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
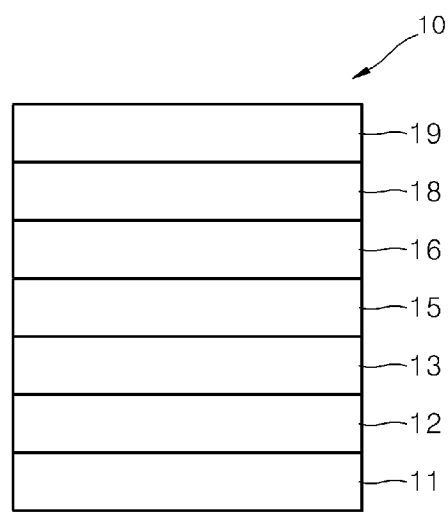
FIG. 1 is a schematic cross-sectional view of an organic light emitting device according to an embodiment of the present invention.

The disclosure will be described more fully hereinafter in the following detailed description of the invention, in which some but not all embodiments of the disclosure are described. This disclosure may be embodied in many different forms and is not to be construed as limited to the embodiments set forth herein; rather, these embodiments are provided so that this disclosure will be thorough and complete, and will fully convey the scope of the invention to those skilled in the art. Like reference numerals refer to like elements throughout.

In the drawings, the thickness of layers, films, panels, regions, etc., are exaggerated for clarity.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer or section. Thus, a first element, component, region, layer, or section discussed below could be termed a second element, component, region, layer, or section without departing from the teachings of the present invention.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

Unless otherwise defined, all terms (including technical and scientific terms) used herein have the same meaning as commonly understood by one of ordinary skill in the art to which this invention belongs.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As used herein, unless otherwise provided, the term "substituted" refers to a compound or radical substituted with at least one (e.g., 1, 2, 3, 4, 5, 6, or more) substituents independently selected from a $C_1$-$C_{30}$ linear or branched alkyl, alkenyl or alkynyl group, a $C_6$ to $C_{18}$ aryl, a halogen (e.g., F, Cl, Br, I), a $C_1$-$C_{30}$ alkoxy group, a lower alkylamino group, a hydroxy group, a nitro group, a cyano group, an amino group, an amidino group, hydrazine, hydrazone, a carboxyl group, a sulfonic acid group, a phosphoric acid group, or the like.

In certain embodiments, a fluoro group-containing compound represented by Formula 1 below is provided.

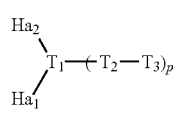

Formula 1

The fluoro group-containing compound may be used as a monomer for synthesizing a polymer represented by Formula 11, herein.

In Formula 1, $Ha_1$ and $Ha_2$ are each independently a halogen atom. For example, $Ha_1$ and $Ha_2$ may be each independently —F, —Cl, or —Br. Both of $Ha_1$ and $Ha_2$ may be —Br, but are not limited thereto.

In Formula 1, $T_1$ is a substituted or unsubstituted $C_6$-$C_{30}$ aromatic group or a substituted or unsubstituted $C_3$-$C_{30}$ heteroaromatic group.

For example, in certain embodiments, $T_1$ may be selected from substituted or unsubstituted benzene, substituted or unsubstituted pentalene, substituted or unsubstituted indene, substituted or unsubstituted naphthalene, substituted or unsubstituted azulene, substituted or unsubstituted heptalene, substituted or unsubstituted indacene, substituted or unsubstituted acenaphthylene, substituted or unsubstituted fluorene, substituted or unsubstituted phenalene, substituted or unsubstituted phenanthrene, substituted or unsubstituted anthracene, substituted or unsubstituted fluoranthene, substituted or unsubstituted triphenylene, substituted or unsubstituted pyrene, substituted or unsubstituted chrysene, substituted or unsubstituted naphthacene, substituted or unsubstituted picene, substituted or unsubstituted perylene, substituted or unsubstituted pentaphene, substituted or unsubstituted hexacene, substituted or unsubstituted pyrrole, substituted or unsubstituted imidazole, substituted or unsubstituted pyrazole, substituted or unsubstituted pyridine, substituted or unsubstituted pyrazine, substituted or unsubstituted pyrimidine, substituted or unsubstituted pyridazine, substituted or unsubstituted isoindole, substituted or unsubstituted indole, substituted or unsubstituted indazole, substituted or unsubstituted purine, substituted or unsubstituted quinoline, substituted or unsubstituted benzoquinoline, substituted or unsubstituted phthalazine, substituted or unsubstituted naphthyridine, substituted or unsubstituted quinoxaline, substituted or unsubstituted quinazoline, substituted or unsubstituted cinnoline, substituted or unsubstituted carbazole, substituted or unsubstituted phenanthridine, substituted or unsubstituted acridine, substituted or unsubstituted phenanthroline, substituted or unsubstituted phenazine, substituted or unsubstituted benzooxazole, substituted or unsubstituted benzoimidazole, substituted or unsubstituted furan, substituted or unsubstituted benzofuran, substituted or unsubstituted thiophene, substituted or unsubstituted benzothiophene, substituted or unsubstituted thiazole, substituted or unsubstituted isothiazole, substituted or unsubstituted benzothiazole, substituted or unsubstituted isoxazole, substituted or unsubstituted oxazole, or substituted or unsubstituted benzooxazole, but is not limited thereto.

In certain embodiments, the substituted aromatic group and substituted heteroaromatic group may include at least one substituent independently selected from a halogen atom, —$CF_3$, —CN, —$Si(A_1)(A_2)(A_3)$, a $C_1$-$C_{30}$ alkyl group, a $C_2$-$C_{30}$ alkenyl group, a $C_6$-$C_{30}$ aryl group, a $C_1$-$C_{30}$ alkoxy group, and an amino group, wherein $A_1$, $A_2$ and $A_3$ are each independently a hydrogen atom, a $C_1$-$C_{30}$ alkyl group, a $C_2$-$C_{30}$ alkenyl group, or a $C_1$-$C_{30}$ alkoxy group. In further embodiments, the substituent may be a halogen atom, —$CF_3$, —CN, —$Si(A_1)(A_2)(A_3)$, a $C_1$-$C_{10}$ alkyl group, a $C_2$-$C_{10}$ alkenyl group, a $C_6$-$C_{14}$ aryl group, a $C_1$-$C_{10}$ alkoxy group, or an amino group, but is not limited thereto.

Representative $T_1$ groups may be selected from a substituted or unsubstituted anthracene ring, a substituted or unsubstituted fluorene ring, a substituted or unsubstituted pyrene ring, and a substituted or unsubstituted chrysene ring, but is not limited thereto. For example, in certain embodiments, $T_1$ may be an anthracene ring, a fluorene ring, a pyrene ring, or a chrysene ring; in further embodiments, $T_1$ may be a fluorene ring.

In Formula 1, $T_2$ is a bivalent linking group represented by —$[C(R_1)(R_2)]_q$—, wherein $R_1$ and $R_2$ may be each independently selected from a hydrogen atom, a halogen atom, a hydroxyl group, an amino group, a cyano group, a carboxylic acid group, a substituted or unsubstituted $C_1$-$C_{30}$ alkyl group, and a substituted or unsubstituted $C_2$-$C_{30}$ alkenyl group, and q is an integer ranging from 1 to about 20. For example, in certain embodiments, $R_1$ and $R_2$ may be each independently selected from a hydrogen atom, a halogen atom, a hydroxyl group, an amino group, a cyano group, a carboxylic acid group, a $C_1$-$C_{10}$ alkyl group, and a $C_2$-$C_{10}$ alkenyl group. In further embodiments, q may be an integer of from about 5 to about 20, but is not limited thereto.

In certain embodiments, at least one —$C(R_1)(R_2)$— of $T_2$ may be replaced by a group independently selected from —O—, —C(=O)—, —S—, a substituted or unsubstituted $C_6$-$C_{30}$ arylene group, and a substituted or unsubstituted $C_3$-$C_{30}$ heteroarylene group. For example, in certain embodiments, at least one —$C(R_1)(R_2)$— may be selectively replaced by —O— or a $C_6$-$C_{14}$ arylene group, (e.g., a phenylene group, a naphthylene group, an anthrylene group, or the like), but is not limited thereto.

In further compounds, $T_2$ may be represented by Formula 2A or 2B, but is not limited thereto.

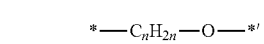

Formula 2A

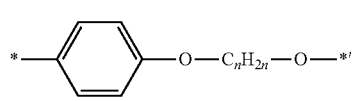

Formula 2B

In Formulae 2A and 2B, * is a binding site to $T_1$ of Formula 1, *' is a binding site to $T_3$ of Formula 1, and n is an integer ranging from 1 to about 10. In certain embodiments, n may be 5, 6, 7, 8, 9, or 10.

In Formula 1, $T_3$ is represented by —$(R_3)_r$—$R_4$. Each $R_3$ may be independently selected from a fluoro group-containing $C_1$-$C_{30}$ alkylene group, a fluoro group-containing $C_2$-$C_{30}$ alkenylene group, a fluoro group-containing $C_6$-$C_{30}$ arylene group, and a fluoro group-containing $C_3$-$C_{30}$ heteroarylene group, $R_4$ is a hydrogen atom, a halogen atom, a hydroxyl group, an amino group, a cyano group, or carboxylic acid, and r is an integer (e.g., ranging from 1 to about 10). Each $R_3$ may be the same as or different from any other $R_3$.

The term "fluoro group-containing", as used herein, refers to a moiety that has at least one covalently bound "—F".

For example, in certain embodiments, $R_3$ may be a fluoro group-containing $C_1$-$C_{10}$ alkylene group or a fluoro group-containing $C_6$-$C_{14}$ arylene group (for example, a fluoro group-containing phenylene group, a fluoro group-containing naphthylene group, a fluoro group-containing anthrylene group or the like). For example, $R_3$ may be selected from a fluoro group-containing methylene group, a fluoro group-containing ethylene group, a fluoro group-containing propylene group, a fluoro group-containing butylene group, a fluoro group-containing phenylene group, a fluoro group-containing naphthylene group, and a fluoro group-containing anthrylene group, but is not limited thereto. In further embodiments, $R_4$ may be a hydrogen atom or a halogen atom (for example, a fluoro group). Within such embodiments, r may be an integer from 1 to 5 (e.g., 1, 2, 3, 4 or 5), but is not limited thereto.

Within certain embodiments, $T_3$ may be represented by Formula 3A or 3B, but is not limited thereto.

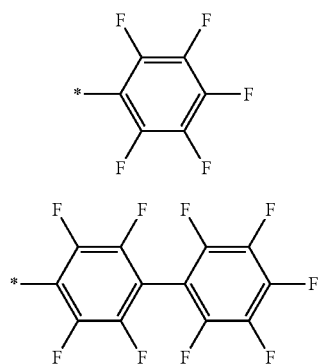

Formula 3A

Formula 3B

In Formulae 3A and 3B, * is a binding site to $T_2$ of Formula 1.

The fluorination degree of $T_3$ may range from about 1% to about 100%, for example, from about 50% to about 100%. The "fluorination degree of $T_3$" is defined by the formula:

(the number of fluoro radicals of $T_3$)/(number of sites in which hydrogen may be present in $T_3$ (i.e., sites in which a fluoro radical could be present))× 100(%).

For example, the fluorination degree of the groups of Formulae 3A and 3B is 100%.

In Formula 1, p is generally an integer ranging from 1 to about 5 (e.g., 1, 2, 3, 4 or 5). The p may be selected based on the structure of $T_1$. In certain embodiments, p is 2 or 3, but is not limited thereto.

Certain fluoro group-containing compounds may be represented by Formula 1A below ($T_1$=fluorene, p=2), but such compounds are not limited thereto.

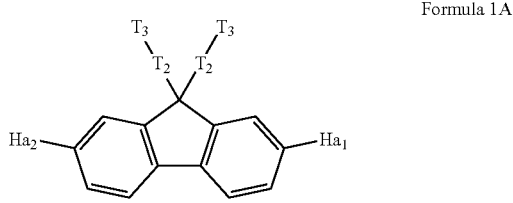

Formula 1A

In Formula 1A, $Ha_1$, $Ha_2$, $T_2$, and $T_3$ are defined as described above. For example, in one embodiment, $T_2$ of Formula 1A may be represented by Formula 2A or 2B; $R_3$ of $T_3$ may be selected from a fluoro group-containing methylene group, a fluoro group-containing ethylene group, a fluoro group-containing propylene group, a fluoro group-containing butylene group, a fluoro group-containing phenylene group, a fluoro group-containing naphthylene group, and a fluoro group-containing anthrylene group, but is not limited thereto, and r is an integer ranging from 1 to about 5; and the fluorination degree of $T_3$ may range from about 50% to about 100%, but these variables are not limited thereto.

In further embodiments, the fluoro group-containing compound may be represented by Formula 1A, $T_2$ may be represented by Formula 2A or 2B, and $T_3$ may be represented by Formula 3A or 3B.

As noted above, within other embodiments, a fluoro group-containing polymer represented by Formula 11 below is provided.

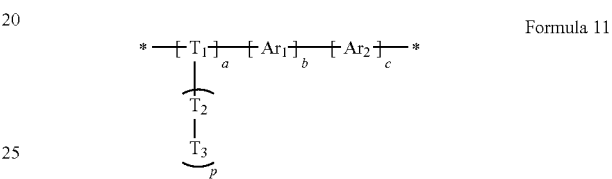

Formula 11

The fluoro group-containing polymer may be contained in an intermediate layer that is interposed between a first electrode and a second electrode of an organic light emitting device. The intermediate layer may be a hole transport layer ("HTL"), and an emission layer ("EML") may be formed on the HTL. Such embodiments of the present invention are discussed in greater detail below.

In Formula 11, $T_1$, $T_2$, $T_3$, and p are defined as described above. It will be apparent that the fluoro group-containing compound represented by Formula 1 may be used as a monomer for synthesizing the fluoro group-containing polymer represented by Formula 11.

In Formula 11, $Ar_1$ and $Ar_2$ are each independently selected from a substituted or unsubstituted $C_6$-$C_{30}$ arylene group; a substituted or unsubstituted $C_3$-$C_{30}$ heteroarylene group; and a system including at least two groups independently selected from substituted or unsubstituted $C_6$-$C_{30}$ arylene groups and substituted or unsubstituted $C_3$-$C_{30}$ heteroarylene groups which two groups are connected to each other by a single bond or by a linking group represented by —N($R_{11}$)—. $R_{11}$ is a hydrogen atom, a substituted or unsubstituted $C_1$-$C_{30}$ alkyl group (e.g., a $C_1$-$C_{10}$ alkyl group), or a substituted or unsubstituted $C_6$-$C_{30}$ aryl group (e.g., a $C_6$-$C_{14}$ aryl group).

For example, within certain embodiments, $Ar_1$ and $Ar_2$ are each independently selected from substituted or unsubstituted phenylene, substituted or unsubstituted pentalenylene, substituted or unsubstituted indenylene, substituted or unsubstituted naphthylene, substituted or unsubstituted azulenylene, substituted or unsubstituted heptalenylene, substituted or unsubstituted indacenylene, substituted or unsubstituted fluorenylene, substituted or unsubstituted phenalenylene, substituted or unsubstituted phenanthrylene, substituted or unsubstituted anthrylene, substituted or unsubstituted fluoranthenylene, substituted or unsubstituted pyrenylene, substituted or unsubstituted chrysenylene, substituted or unsubstituted picenylene, substituted or unsubstituted perylenylene, substituted or unsubstituted pyrrolylene, substituted or unsubstituted imidazolylene, substituted or unsubstituted pyrazolylene, substituted or unsubstituted pyridinylene, substituted or unsubstituted pyrazinylene, substituted or unsubstituted pyrimidinylene, substituted or unsubstituted pyridazinylene, substituted or unsubstituted isoindolylene, substituted or unsubstituted indolylene, substituted or unsubstituted indazolylene, substituted or unsubstituted purinylene, substituted or unsubstituted quinolinylene, substituted or unsubstituted benzoquinolinylene, substituted or unsubstituted phthalazinylene, substituted or unsubstituted naphthyridinylene, substituted or unsubstituted quinoxalinylene, substituted or unsubstituted quinazolinylene, substituted or unsubstituted cinnolinylene, substituted or unsubstituted carbazolylene, substituted or unsubstituted phenanthridinylene, substituted or unsubstituted acridinylene, substituted or unsubstituted phenanthrolinylene, substituted or unsubstituted phenazinylene, substituted or unsubstituted benzothiazolylene, substituted or unsubstituted benzooxazolylene, substituted or unsubstituted benzoimidazolylene, substituted or unsubstituted puranylene, substituted or unsubstituted benzopuranylene, substituted or unsubstituted thiophenylene, substituted or unsubstituted benzothiophenylene, substituted or unsubstituted thiazolylene, substituted or unsubstituted isothiazolylene, substituted or unsubstituted isoxazolylene, substituted or unsubstituted oxazolylene, substituted or unsubstituted benzo-oxazolylene, groups represented by any one of Formulae 12A to 12G, and a system including at least two groups independently selected from the foregoing which are connected to each other by a single bond or a linking group represented by —N($R_{11}$)—, wherein $R_{11}$ is a $C_1$-$C_{10}$ alkyl group or a $C_6$-$C_{14}$ aryl group.

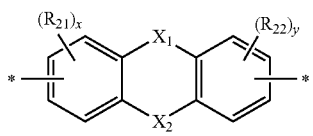

Formula 12A

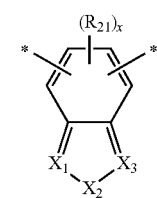

Formula 12B

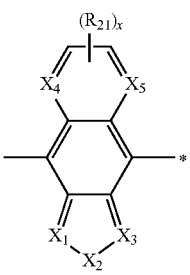

Formula 12C

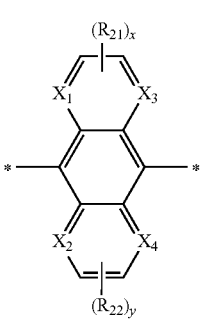

Formula 12D

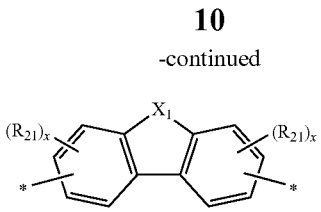

Formula 12E

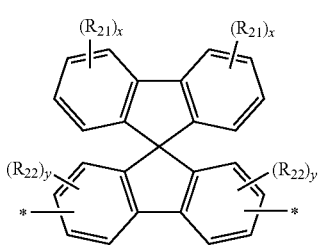

Formula 12F

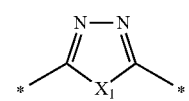

Formula 12G

In Formulae 12A to 12G, $X_1$ to $X_5$ are each independently selected from O, S, C(=O), N($R_{25}$), and C($R_{25}$)($R_{26}$); $R_{21}$, $R_{22}$, $R_{25}$ and $R_{26}$ are each independently selected from a hydrogen atom, a substituted or unsubstituted $C_1$-$C_{30}$ alkyl group (e.g., a $C_1$-$C_{10}$ alkyl group), a substituted or unsubstituted $C_1$-$C_{30}$ alkoxy group (e.g., a $C_1$-$C_{10}$ alkoxy group), and a substituted or unsubstituted $C_6$-$C_{30}$ aryl group (e.g., a $C_6$-$C_{14}$ aryl group; or a $C_6$-$C_{14}$ aryl group substituted with at least one $C_1$-$C_{30}$ alkyl group, $C_1$-$C_{30}$ alkoxy group, $C_2$-$C_{30}$ alkenyl group, or $C_6$-$C_{30}$ aryl group); and x and y are each independently an integer ranging from 1 to about 4 (e.g., 1, 2, 3 or 4).

For example, in certain embodiments $Ar_1$ and $Ar_2$ may be each independently selected from compounds represented by any one of Formulae 13A through 13T below, but these variables are not limited thereto:

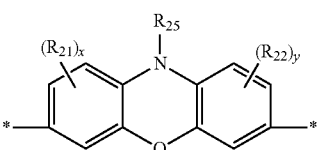

Formula 13A

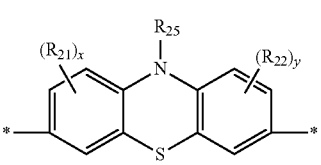

Formula 13B

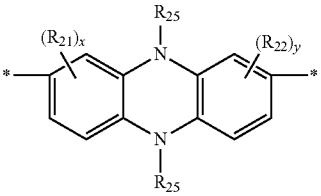

Formula 13C

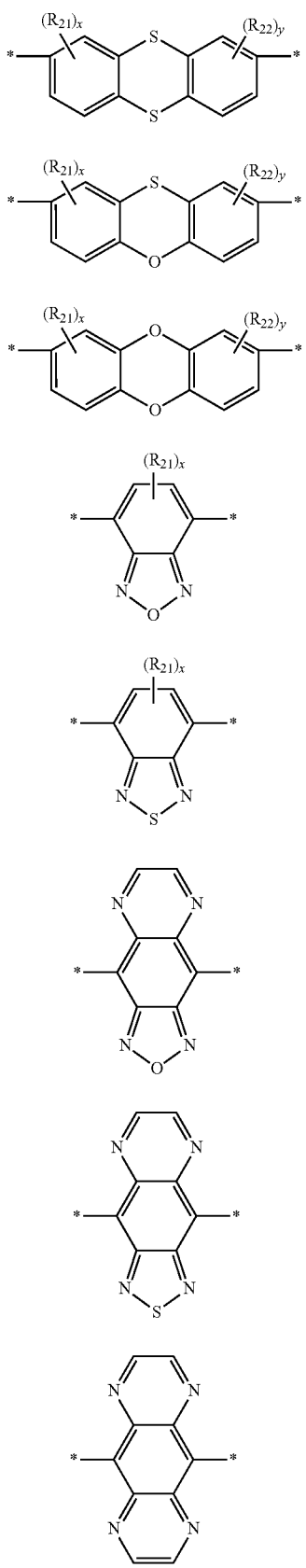
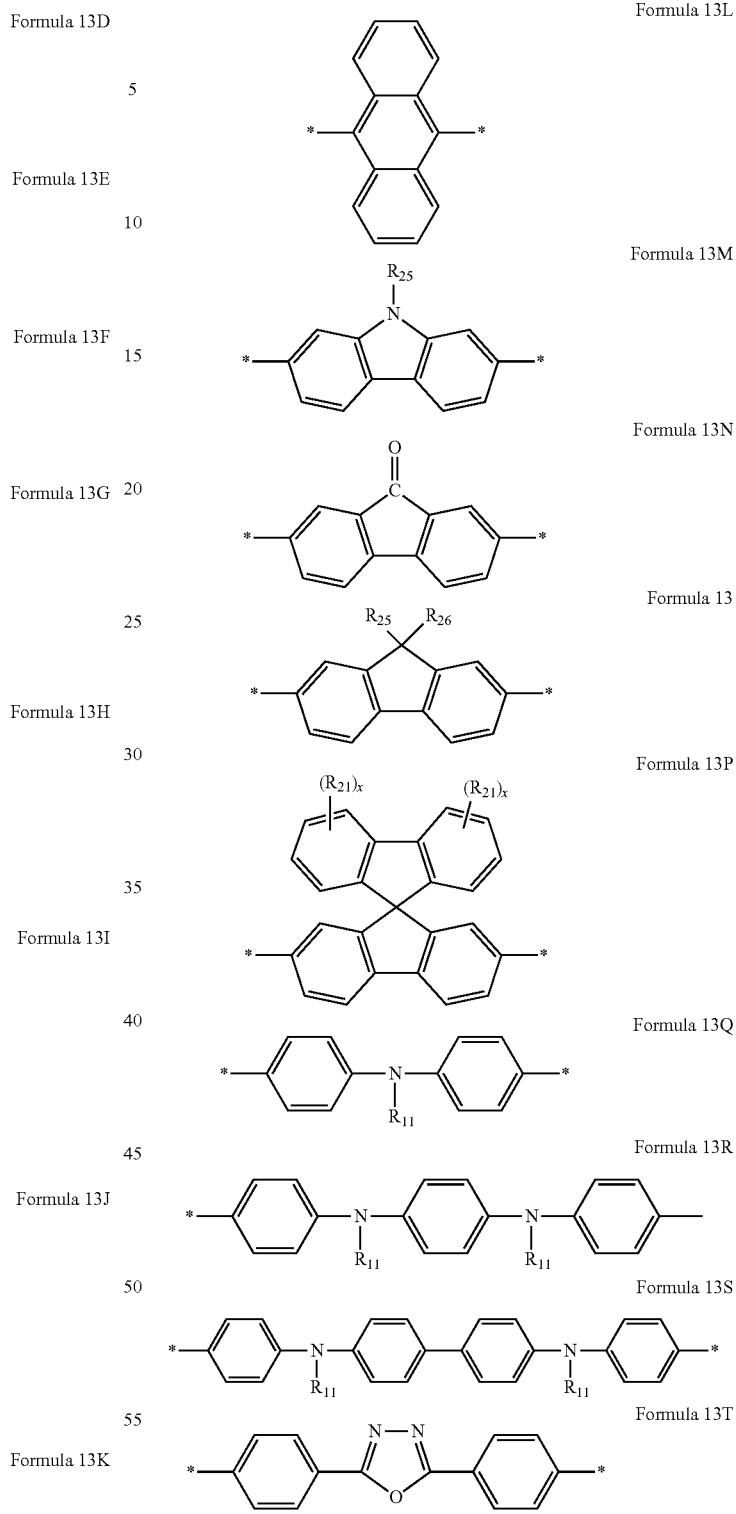

In Formulae 13A to 13T, $R_{21}$, $R_{22}$, $R_{25}$ and $R_{26}$ are each independently selected from a hydrogen atom; a $C_1$-$C_{10}$ alkyl group; a $C_1$-$C_{10}$ alkoxy group; a $C_6$-$C_{14}$ aryl group; and a $C_6$-$C_{14}$ aryl group substituted with at least one $C_1$-$C_{30}$ alkyl group, $C_1$-$C_{30}$ alkoxy group, $C_2$-$C_{30}$ alkenyl group, and $C_6$-$C_{30}$ aryl group; x is an integer ranging from 1 to about 4; and $R_{11}$ is a $C_1$-$C_{10}$ alkyl group or a $C_6$-$C_{14}$ aryl group.

For example, in certain embodiments one or more of $Ar_1$ and $Ar_2$ may be represented by Formula 14A below.

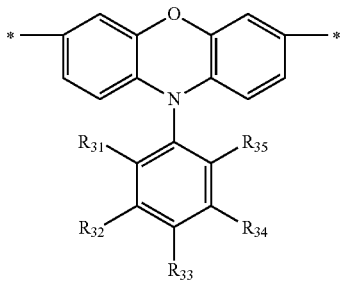

Formula 14A

In Formula 14A, $R_{31}$ to $R_{35}$ are each independently selected from a hydrogen atom, a $C_1$-$C_{30}$ alkyl group, a $C_1$-$C_{30}$ alkoxy group, a $C_2$-$C_{30}$ alkenyl group, and a $C_6$-$C_{30}$ aryl group. For example, in certain embodiments, $R_{31}$ to $R_{35}$ may be each independently a hydrogen atom; a $C_1$-$C_{10}$ alkyl group; or a $C_1$-$C_{10}$ alkoxy group, but these variables are not limited thereto. For example, in certain compounds of Formula 14A, $R_{31}$, $R_{32}$, $R_{34}$, and $R_{35}$ may be each independently a hydrogen atom, and $R_{33}$ may be a $C_1$-$C_{10}$ alkyl group or a $C_1$-$C_{10}$ alkoxy group.

In Formula 11, a, b, and c may be each independently a real number satisfying $0<a\leq0.99$, $0<b\leq0.99$, and $0\leq c\leq0.99$, and a+b+c=1. If c is 0, the fluoro group-containing polymer may be a copolymer. If c is not 0, the fluoro group-containing polymer may be a terpolymer.

For example, in certain embodiments, in the fluoro group-containing polymer, c may be 0; and $Ar_1$ may be a group represented by any one of Formulae 13A to 13T.

In other embodiments of the fluoro group-containing polymer, c may be 0; and $Ar_1$ may be represented by Formula 14A. In certain such polymers, $T_1$ may be fluorene; $T_2$ may be represented by Formula 2A or 2B; $R_3$ of $T_3$ may be selected from a fluoro group-containing methylene group, a fluoro group-containing ethylene group, a fluoro group-containing propylene group, a fluoro group-containing butylene group, a fluoro group-containing phenylene group, a fluoro group-containing naphthylene group, and a fluoro group-containing anthrylene group, and r is an integer ranging from 1 to about 5; and the fluorination degree of $T_3$ may range from about 50% to about 100%, but these variables are not limited thereto.

Certain fluoro group-containing polymer may also be represented by Formula 11A below.

In Formula 11A, $T_2$ is represented by Formula 2A or 2B, wherein * is a binding site to a fluorene ring of Formula 11A and *' is a binding site to a fluoro group-containing phenyl group of Formula 11A; $R_{31}$ to $R_{35}$ are each independently selected from a hydrogen atom, a $C_1$-$C_{30}$ alkyl group (for example, $C_1$-$C_{10}$ alkyl group), a $C_1$-$C_{30}$ alkoxy group (for example, $C_1$-$C_{10}$ alkoxy group), a $C_2$-$C_{30}$ alkenyl group (for example, $C_2$-$C_{10}$ alkenyl group), and a $C_6$-$C_{30}$ aryl group (for example, $C_6$-$C_{14}$ aryl group); and a and b are each independently a real number satisfying $0<a\leq0.99$ and $0<b\leq0.99$, and a+b=1.

Certain fluoro group-containing polymers represented by Formula 11 may have a number average molecular weight ranging from about 10000 to about 300000 based on that of polystyrene and a polydispersity index ("PDI") ranging from about 1.5 to about 5, but these ranges are not limited thereto. The number average molecular weight and the PDI may be selected by considering the structure of an organic light emitting device including the fluoro group-containing polymer or characteristics of the organic light emitting device.

Since the fluoro group-containing polymer contains "$T_3$" as defined above, it may be substantially insoluble in a solvent. For example, certain fluoro group-containing polymers are substantially insoluble in toluene or xylene. When an intermediate layer including such a fluoro group-containing polymer is formed, and then a composition including toluene or xylene, as a solvent, is provided onto the intermediate layer, the intermediate layer is substantially insoluble in the solvent, e.g., toluene or xylene. This property may be advantageous when the polymer is incorporated into an organic light emitting device. In addition, the fluoro group-containing polymer has excellent electrical properties.

Thus, the fluoro group-containing polymer may be efficiently used in an organic light emitting device manufactured based on a wet process. This will be described in more detail with reference to a method of manufacturing an organic light emitting device.

Throughout the specification, nonlimiting examples of the unsubstituted $C_1$-$C_{30}$ alkyl group include a methyl group, an ethyl group, a propyl group, an isobutyl group, a sec-butyl, a pentyl group, an iso-amyl group, and a hexyl group. In the $C_1$-$C_{30}$ alkyl group, in certain embodiments, at least one of the hydrogen atoms may be substituted with a halogen atom, a $C_1$-$C_{30}$ alkyl group, a $C_1$-$C_{30}$ alkoxy group, a lower alky-

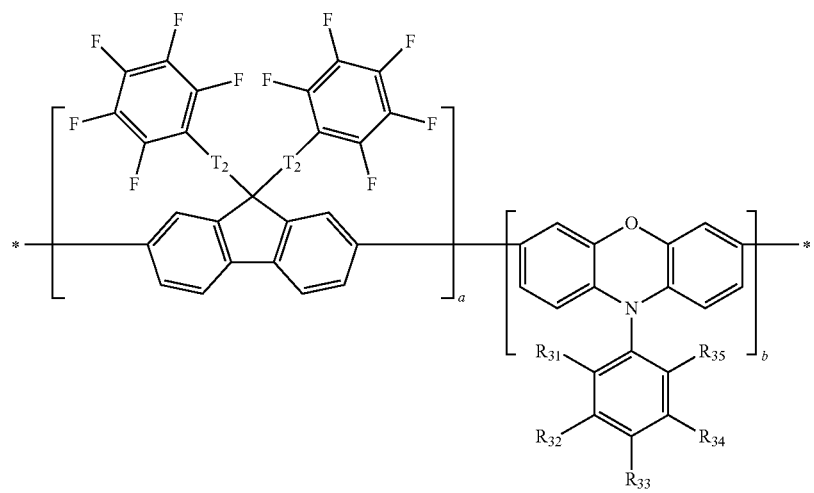

Formula 11A lamino group, a hydroxy group, a nitro group, a cyano group, an amino group, an amidino group, hydrazine, hydrazone, a carboxyl group, a sulfonic acid group, a phosphoric acid group, or the like.

Throughout the specification, nonlimiting examples of the unsubstituted $C_2$-$C_{30}$ alkenyl group include an ethenyl group. In the $C_2$-$C_{30}$ alkenyl group of certain embodiments, at least one of the hydrogen atoms may be substituted with one or more substituents as described above in connection with the $C_1$-$C_{30}$ alkyl group.

Throughout the specification, nonlimiting examples of the unsubstituted $C_1$-$C_{30}$ alkoxy group include a methoxy group, an ethoxy group, a propoxy group, an isobutyloxy group, a sec-butyloxy group, a pentyloxy group, an iso-amyloxy group, and a hexyloxy group. In the $C_1$-$C_{30}$ alkoxy group of certain embodiments, at least one of the hydrogen atoms may be substituted with one or more substituents as described above in connection with the $C_1$-$C_{30}$ alkyl group.

Throughout the specification, the $C_6$-$C_{30}$ aryl group refers to a monovalent carbocyclic system that comprises one or more rings with all ring members being carbon, at least one of which rings is aromatic. If the $C_6$-$C_{30}$ aryl group includes two or more rings, these rings may be pendent or spiro, or may be fused together. Representative aryl groups include, for example, phenyl, naphthyl, and tetrahydronaphthyl. In the aryl group, at least one of the hydrogen atoms may be substituted with the substituents described above in connection with the $C_1$-$C_{30}$ alkyl group.

Throughout the specification, the $C_3$-$C_{30}$ heteroaromatic group refers to a monovalent group that comprises one or more rings, at least one of which is aromatic, and at least one of which comprises at least one heteroatom (e.g., 1, 2 or 3 heteroatoms) such that the total number of ring carbon atoms ranges from 3 to 30. The heteroatom(s) are generally independently chosen from nitrogen (N), oxygen (O), phosphorous (P) and sulfur (S). In certain representative embodiments, the total number of ring heteroatoms ranges from 1 to 10; in further representative embodiments, the $C_3$-$C_{30}$ heteroaromatic group comprises from 5 to 35 total ring atoms. When the $C_3$-$C_{30}$ heteroaromatic group has two or more rings, these rings may be pendent or spiro, or fused together. Nonlimiting examples of a heteroaromatic group include pyridyl, thienyl, and furyl. In the heteroaromatic group, at least one of the hydrogen atoms may be replaced with a substituent as described above in connection with the $C_1$-$C_{30}$ alkyl group.

Throughout the specification, the $C_6$-$C_{30}$ arylene group is a bivalent linking group having the same structure as that of the $C_6$-$C_{30}$ aryl group, and the $C_3$-$C_{30}$ heteroarylene group is a bivalent linking group having the same structure as that of the $C_3$-$C_{30}$ heteroaromatic group. Examples of the $C_6$-$C_{30}$ arylene group and the $C_3$-$C_{30}$ heteroarylene group will be apparent to those skilled in the art with reference to examples of the $C_6$-$C_{30}$ aryl group and the $C_3$-$C_{30}$ heteroaromatic group described above.

The fluoro group-containing polymer represented by Formula 11 may be synthesized by known methods in the art such as Suzuki coupling or Yamamoto coupling, which will be obvious to those skilled in the art with reference to examples described hereinafter.

Within other embodiments, an organic light emitting device including: a substrate; a first electrode; a second electrode; an intermediate layer that is interposed between the first electrode and the second electrode and including a fluoro group-containing polymer represented by Formula 11; and an emission layer ("EML") that is formed close to the intermediate layer is provided.

In one embodiment, the intermediate layer may function as a HTL.

In a further embodiment, the EML may comprise a polymer represented by Formula 21 below, but is not limited thereto.

Formula 21

In Formula 21, $Ar_{11}$ and $Ar_{12}$ are each independently selected from a substituted or unsubstituted $C_6$-$C_{30}$ arylene group; a substituted or unsubstituted $C_3$-$C_{30}$ heteroarylene group; and a system including at least two groups independently selected from a substituted or unsubstituted $C_6$-$C_{30}$ arylene group and a substituted or unsubstituted $C_3$-$C_{30}$ heteroarylene group, which two groups are connected to each other by a single bond or by a linking group represented by —N($R_{51}$)—, wherein $R_{51}$ is a hydrogen atom, a substituted or unsubstituted $C_1$-$C_{30}$ alkyl group, or a substituted or unsubstituted $C_6$-$C_{30}$ aryl group; and d and e are each independently a real number satisfying $0<d\leq0.99$ and $0<e\leq0.99$, and $d+e=1$. Each "*" indicates a point of attachment to the same or a different polymeric unit represented by Formula 21.

In certain embodiments of Formula 21, $Ar_{11}$, $Ar_{21}$, and $R_{51}$ are defined as described above in connection with $Ar_1$, $Ar_2$, and $R_{11}$, respectively.

In an embodiment, the EML may include a polymer represented by Formula 21A or 21B, but is not limited thereto.

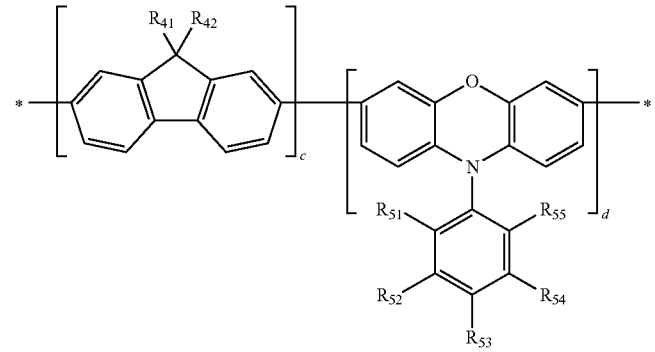

Formula 21A

Formula 21B

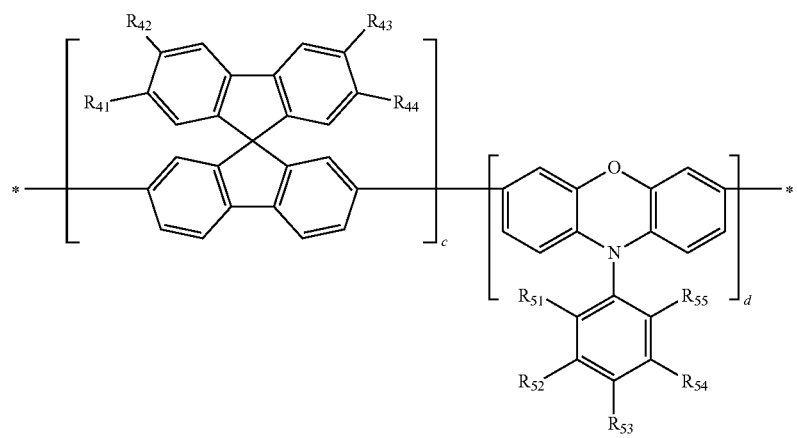

In Formula 21A and 21B, $R_{41}$ to $R_{44}$ are defined as described above in connection with $R_{21}$, and $R_{51}$ to $R_{55}$ are defined as described above in connection with $R_{31}$.

In certain embodiments, $R_{41}$ to $R_{44}$ in Formula 21A and 21B may be each independently a hydrogen atom, a $C_1$-$C_{10}$ alkyl group, a $C_1$-$C_{10}$ alkoxy group (e.g., —$OC_8H_{17}$), or a $C_6$-$C_{14}$ aryl group (e.g., a phenyl group or naphthyl group), but these variables are not limited thereto.

In further embodiments of Formulae 21A and 21B, $R_{51}$, $R_{52}$, $R_{54}$, and $R_{55}$ may be each independently a hydrogen atom, and $R_{53}$ may be a $C_1$-$C_{10}$ alkoxy group (e.g., —$OC_8H_{17}$), but these variables are not limited thereto.

Certain organic light emitting devices may further include at least one layer selected from a hole injection layer ("HIL"), a hole blocking layer ("HBL"), an electron transport layer ("ETL"), and an electron injection layer ("EIL") between the first electrode and the second electrode in addition to the intermediate layer, for example, functioning as a HTL, and the EML.

A method of manufacturing an organic light emitting device according to an embodiment of the present invention may comprise: forming a first electrode on a substrate; forming an intermediate layer comprising a fluoro group-containing polymer represented by Formula 11 by applying a first composition for forming an intermediate layer comprising the fluoro group-containing polymer represented by Formula 11 and a first solvent to the first electrode, and baking the first composition at a temperature for a time period suitable for removing the first solvent; forming an EML by applying a second composition for forming an EML comprising an EML-forming material and a second solvent to the intermediate layer, and heat-treating the second composition; and forming a second electrode on the EML.

The fluoro group-containing polymer represented by Formula 11 may, in certain embodiments, be substantially insoluble in the second solvent contained in the second composition.

Throughout the specification, "the fluoro group-containing polymer is substantially insoluble in the second solvent" means that 10 wt % or less of the fluoro group-containing polymer of Formula 11 dissolves in the second solvent in a standard state (at 1 atm and at 25° C.), so that an intermixing layer, in which the fluoro group-containing polymer and the EML forming material are mixed, is not substantially formed between the intermediate layer including the fluoro group-containing polymer of Formula 11 and the EML.

In other organic light emitting devices, an intermixing layer can be formed in an interface between an intermediate layer and an EML since at least one portion of the intermediate layer that is already formed is dissolved in a solvent contained in the EML forming composition when the EML is formed using a wet process. In order to prevent the formation of an intermixing layer, cross-linking is sometimes induced when an intermediate layer is formed by introducing a cross-linkable group into the first composition for forming the intermediate layer and performing the heat-treatment at a temperature at which the cross-linking is performed (e.g., at 200° C. or higher). However, characteristics of the intermediate layer including the cross-linked resultant are not easily controlled, and the resulting electrical characteristics may not be satisfactory.

Use of the polymer of Formula 11 may avoid this problem since, in certain embodiments, is substantially insoluble in the second solvent contained in the second composition. As a result, at least one portion of the intermediate layer is not substantially dissolved in the second solvent for the second composition, even though cross-linking is not induced in the formation of the intermediate layer. In other words, the polymer of Formula 11 substantially remains in the intermediate layer formed by applying the first composition comprising the polymer of Formula 11 and the first solvent to the first electrode and baking the first composition, even when the intermediate layer and the EML are formed using a wet process. Thus, an intermixing layer is not formed between the intermediate layer and the EML, and the thickness of the intermediate layer may be maintained.

Within such embodiments, there is no need for a cross-linking step in order to prevent the formation of an intermixing layer in the interface between the intermediate layer and the EML when the intermediate layer of the organic light emitting device is formed. As a result, the organic light emitting device described herein may be simply manufactured and have excellent electrical characteristics.

In certain embodiments, about 8 wt % or less, about 6 wt % or less, about 4 wt % of less, about 2 wt % or less, about 1 wt % or less, about 0.5 wt % or less, about 0.1 wt % or less, about 0.05 wt % or less, or about 0.001 wt % or less of the fluoro group-containing polymer of Formula 11 based on 100 wt % of the fluoro group-containing polymer may be soluble in the second solvent in a standard state (at 1 atm and at 25□). For example, the fluoro group-containing polymer represented by Formula 11 may be insoluble, i.e., completely insoluble, in the second solvent in a standard state (at 1 atm and at 25° C.).

The first solvent present in the first composition may be chloroform, tetrahydrofuran, chlorobenzene, or the like, but is not limited thereto. The first solvent may also be any combination of at least two of the solvents. The second solvent present in the second composition may be toluene, xylene, or the like, but is not limited thereto. The second solvent may also be any combination of at least two of the solvents.

After providing the first composition including the fluoro group-containing polymer and the first solvent, conditions such as temperature and time period for baking to form the intermediate layer may be selected such that the first solvent is removed. The "baking" used herein refers to a heat-treatment that is performed at a temperature for a time period by which the solvent contained in a film forming composition is removed, but the other components are not substantially deformed (e.g., deformation (polymerization) of the compound by the cross-linking).

The conditions for the baking for forming the intermediate layer may vary according to the boiling point and the amount of the first solvent. For example, in certain embodiments, the baking may be performed at a temperature ranging from about 130° C. to about 200° C. for about 10 minutes to about 60 minutes.

After the second composition including the EML forming material and the second solvent is provided onto the intermediate layer, the heat-treatment to form the EML may be performed under the same conditions as those of the baking as described above or under conditions for inducing cross-linking between the EML-forming materials. The conditions for the heat-treatment to form the EML may vary according to the EML-forming material and the second solvent.

FIG. 1 is a schematic cross-sectional view of an organic light emitting device 10 according to an embodiment of the present invention. The organic light emitting device 10 includes a substrate 11, a first electrode 12, a HIL 13, an intermediate layer 15, an EML 16, an EIL 18, and a second electrode 19. The intermediate layer 15 may function as a HTL.

The organic light emitting device 10 comprises A first electrode material having a high work function, which may be formed on the substrate 11 using deposition, ion-plating, plating, sputtering, or the like to form the first electrode 12. The first electrode 12 may be an anode capable of injecting holes or a cathode capable of injecting electrons. The substrate 11 may be any substrate that is used in conventional organic light emitting devices, such as a glass substrate or a transparent plastic substrate with suitable mechanical strength, thermal stability, transparency, surface smoothness, ease of handling and waterproofness. A metal oxide, metal sulfate, or metal that exhibits a high electrical conductivity may be used as the first electrode material in a thin film form. Exemplary first electrode materials include indium oxide, zinc oxide, tin oxide, indium tin oxide ("ITO"), indium zinc oxide ("IZO"), gold (Au), platinum (Pt), silver (Ag), copper (Cu), or the like. In addition, polyaniline or derivatives thereof and polythiophene or derivatives thereof may be used as the first electrode material. The first electrode 12 may have a single or multi-layer structure and may include two different types of materials. The thickness of the first electrode 12 may vary according to the transmittance of light and electrical conductivity. For example, the first electrode 12 may have a thickness ranging from about 10 nm to about 10 μm.

If the first electrode 12 is an anode, the HIL 13 is formed on the first electrode 12. The HIL 13 may be formed on the first electrode 12 using various methods known in the art, such as vacuum deposition, spin coating, casting, inkjet printing and Langmuir-Blodget (LB) deposition.

If the HIL 13 is formed using vacuum deposition, the deposition conditions may vary according to the compound(s) used to form the HIL 13, and the structure and thermal properties of the HIL 13 to be formed. In general, however, representative conditions for vacuum deposition may include a deposition temperature ranging from about 100 to about 500° C., a pressure ranging from about $10^{-8}$ to about $10^{-3}$ torr, and a deposition velocity ranging from about 0.01 to about 100° C./sec.

When forming the HIL 13 by spin coating, the coating conditions may vary according to the compound(s) used as the material for the HIL 13. A representative coating speed ranges from about 2000 to 5000 rpm, and a representative heat-treatment temperature for removing a solvent after coating ranges from about 80 to 300° C.

The HIL 13 may be formed of any material that is commonly used to form a HIL. Examples of materials that may be used to form the HIL 13 include a phthalocyanine compound such as copper phthalocyanine, 4,4',4"-tris(3-methylphenylphenylamino) triphenylamine ("m-MTDATA"), N,N'-di (1-naphthyl)-N,N'-diphenylbenzidine ("NPB"), TDATA (see a formula below), 2T-NATA (see a formula below), polyaniline/dodecylbenzenesulfonic acid ("Pani/DBSA"), poly(3,4-ethylenedioxythiophene)/poly(4-styrene sulfonate) ("PEDOT/PSS"), polyaniline/camphor sulfonic acid ("Pani/CSA"), and polyaniline/poly(4-styrene sulfonate) ("PANI/PSS"), but the material used to form the HIL 13 is not limited thereto.

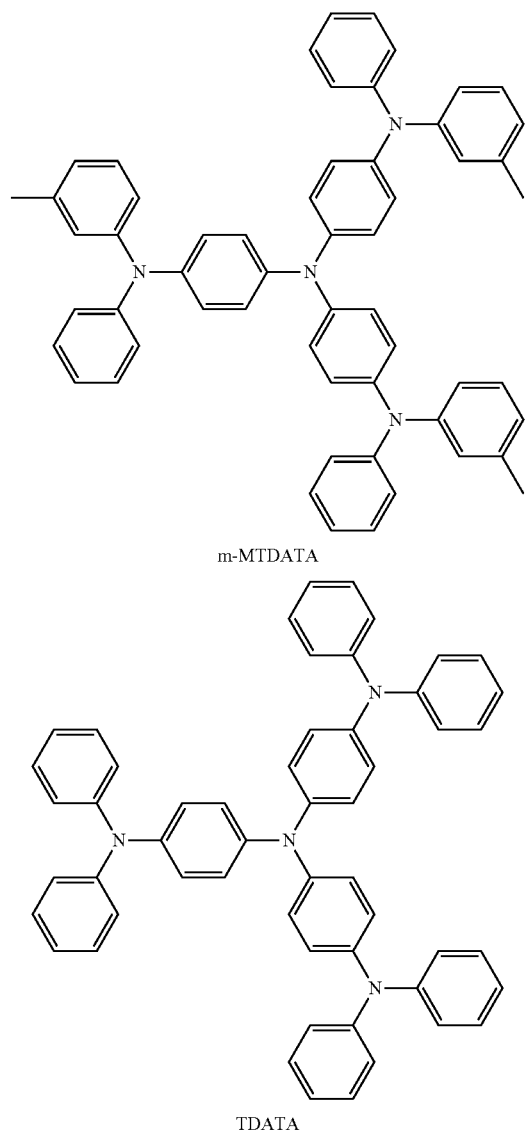

m-MTDATA

TDATA

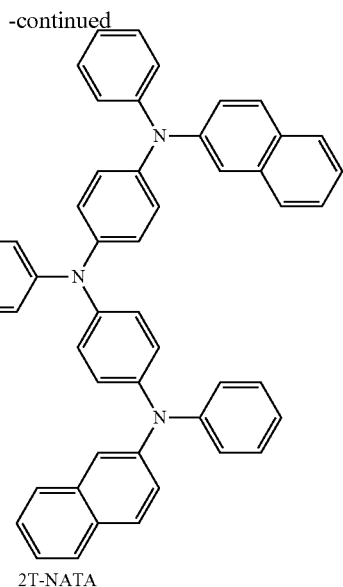

2T-NATA

The thickness of an HIL 13 may be in the range of about 100 to about 10000 Å, and for example, about 100 to about 1000 Å. When the thickness of the HIL 13 is within the above range, the HIL 13 may have excellent hole injection properties without an increase in driving voltage.

An intermediate layer 15 that comprises the fluoro group-containing polymer represented by Formula 11 may be formed on the HIL 13. The intermediate layer 15 may function as a HTL. The intermediate layer 15 may be formed by providing the first composition for forming an intermediate layer (wherein the first composition comprises the fluoro group-containing polymer represented by Formula 11 and the first solvent) onto the HIL 13, and baking the first composition at a temperature for a time period suitable for removing the first solvent and forming a film of the intermediate layer 15. The first composition may be formed on the HIL 13 by any known method, such as spin coating, casting, and inkjet printing. The first solvent and the conditions for the baking are described above.

The thickness of the intermediate layer 15 functioning as the HTL may be in the range of about 50 to 1,000 Å, for example, about 100 to about 600 Å. When the thickness of the HTL is within this range, the HTL may have excellent hole transporting ability without a substantial increase in driving voltage. In addition, since the intermediate layer 15 is not substantially dissolved in the second solvent contained in the second composition for forming an EML, the thickness of the intermediate layer 15 may be maintained after the EML 16 is formed.

The EML 16 may be formed on the HTL by spin coating, casting, inkjet printing, Langmuir-Blodgett (LB) deposition, or the like. When the EML 16 is formed using spin coating, the conditions for the coating are generally similar to those for the formation of the HIL 13, although the conditions for coating may vary according to the material that is used to form the EML 16.

In an embodiment, the EML 16 may include the polymer represented by Formula 21 as described above.

In certain embodiments, the thickness of the EML 16 may be in the range of about 100 to about 1,000° C., for example, about 300 to about 900° C. When the thickness of the EML 16 is within the above range, the EML 16 may have excellent emission characteristics without a substantial increase in driving voltage.

Within further embodiments, although not shown in FIG. 1, a HBL and an ETL may further be formed on the EML 16.

The HBL may prevent diffusion of triplet excitons or holes of the EML 16 into the second electrode 19, or the like. The HBL may be formed by any technique known in the art, such as vacuum deposition, spin coating, casting, LB deposition, or the like. When the HBL is formed by vacuum deposition or spin coating, the deposition and coating conditions may be similar to those for formation of the HIL 13, although the deposition and coating conditions may vary according to the compound(s) used to form the HBL. In certain embodiments, for example, one or more of oxadiazole derivatives, triazole derivatives, phenanthroline derivatives or BCP may be used to form the HBL.

The thickness of the HBL may be in the range of about 50 to about 1000 Å, for example, about 100 to about 300 Å. When the thickness of the HBL is within the range described above, the HBL may have excellent hole blocking properties.

The ETL may be formed on the HBL or EML using various methods such as vacuum deposition, spin coating, or casting. When the ETL is formed using vacuum deposition or spin coating, the deposition and coating conditions may be similar to those for formation of the HIL 13, although the deposition and coating conditions may vary according to the compound(s) used to form the ETL. The ETL forming material may be any known material that stably transports electrons injected from an electron injection electrode, that is, a cathode. For example, the ETL forming material may be a quinoline derivative or 4,7-diphenyl-1,10-phenanthroline ("Bphen").

The thickness of the ETL may be in a range of about 100 to about 1,000 Å, for example, about 200 to about 500 Å. If the thickness of the ETL is within the above range, the ETL may have excellent electron transport properties without a substantial increase in driving voltage.

The EIL 18 may be formed on the EML 16. The EIL 18 may be formed of LiF, NaCl, CsF, $Li_2O$, BaO, $BaF_2$, or any other suitable material known in the art. Deposition conditions are similar to those for formation of the HIL 13, although the deposition conditions may vary according to the material that is used to form the EIL 18.

The thickness of the EIL 18 may be in a range of about 1 to about 100 Å, for example, about 5 to about 50 Å. When the thickness of the EIL 18 is within the range described above, an excellent electron injection ability of the EIL 18 may be obtained without a substantial increase in driving voltage.

Finally, the second electrode 19 may be formed on the EIL 18. The second electrode 19 may be formed as described above for the first electrode 12. The second electrode 19 may be a cathode or an anode. If the second electrode 19 is used as a cathode, a low work function material may be used. For example, an alkali metal such as lithium (Li), sodium (Na), potassium (K), rubidium (Rb), and cesium (Cs); an alkaline earth metal such as beryllium (Be), magnesium (Mg), calcium (Ca), strontium (Sr), and barium (Ba); metal such as aluminum (Al), scandium (Sc), vanadium (V), zinc (Zn), yttrium (Y), indium (In), cerium (Ce), samarium (Sm), europium (Eu), terbium (Tb), and ytterbium (Yb); an alloy formed of at least two thereof; an alloy formed of at least one of the elements described above and at least one element selected from gold (Au), silver (Ag), platinum (Pt), copper (Cu), manganese (Mn), titanium (Ti), cobalt (Co), nickel (Ni), tungsten (W), and tin (Sn); graphite; or graphite interlayer compounds may be used. The alloy may be Mg—Ag alloy, Mg—In alloy, Mg—Al alloy, In—Ag alloy, Li—Al alloy, Li—Mg alloy, Li—In alloy, Ca—Al alloy or the like. In addition, the second electrode 19 may have a single layer or at least two layers. The second electrode 19 may include a single material or at least two materials, and may be a transparent, semitransparent, or reflective electrode. The thickness of the second electrode 19 may be in the range of about 10 nm to about 10 μm but is not limited thereto.

Hereinafter, one or more embodiments of the present invention will be described in detail with reference to the following examples. However, these examples are not intended to limit the purpose and scope of this disclosure.

EXAMPLES

Synthesis Example 1

Synthesis of Compound 1

Compound 1 was synthesized through Reaction Scheme 1 below:

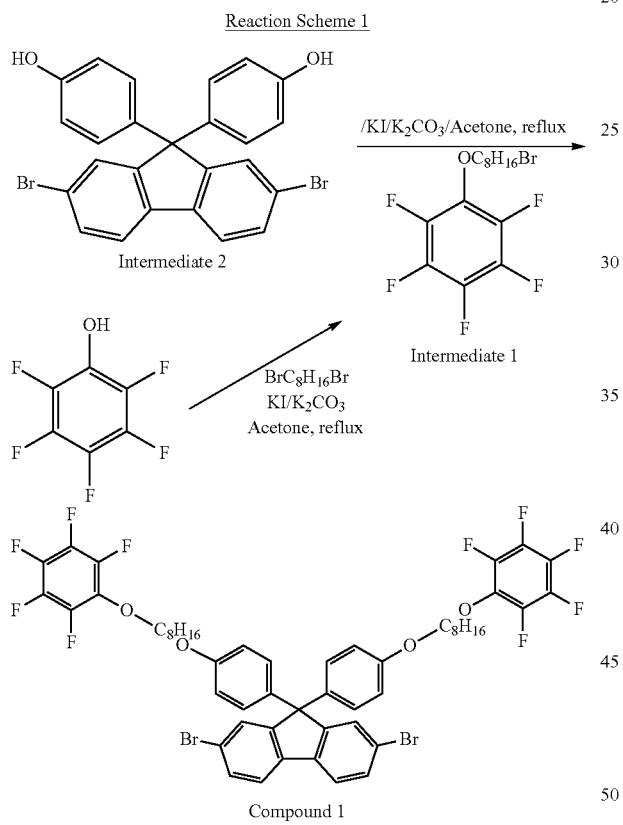

Reaction Scheme 1

Compound 1

(1) Synthesis of Intermediate 1

10 g of pentafluorophenol, 73.9 g of 1,8-dibromooctane (5 equivalents), potassium iodide (0.05 equivalents based on pentafluorophenol), and potassium carbonate (3 equivalents based on pentafluorophenol) were mixed. After the reaction was terminated, the resultant was distilled and purified to obtain Intermediate 1 (yield: 67.5%), and the structure of the product was identified using $^1$H-NMR.

(2) Synthesis of Compound 1

3.5 g of fluorene-based diol, as Intermediate 2, 5.7 g of Intermediate 1 (2.2 equivalents), potassium iodide (0.05 equivalents based on Intermediate 2), and potassium carbonate (3 equivalents based on Intermediate 2) were mixed. After the reaction was terminated, the resultant was purified using column chromatography (ethyl acetate (EA):hexane=1:40) to obtain 5.1 g of Compound 1 (yield: 68%), and the structure of the product was identified using $^1$H-NMR.

$^1$H-NMR (300 MHz, CDCl$_3$): δ 1.29 (m, 16H), δ1.71 (m, 4H), δ1.74 (m, 4H), δ3.94 (t, 4H), δ4.06 (m, 4H), δ6.65 (d, 4H), δ6.95 (d, 4H), δ7.5~7.7 (m, 6H)

Synthesis Example 2

Synthesis of Compound 2

Compound 2 was synthesized through Reaction Scheme 2 below:

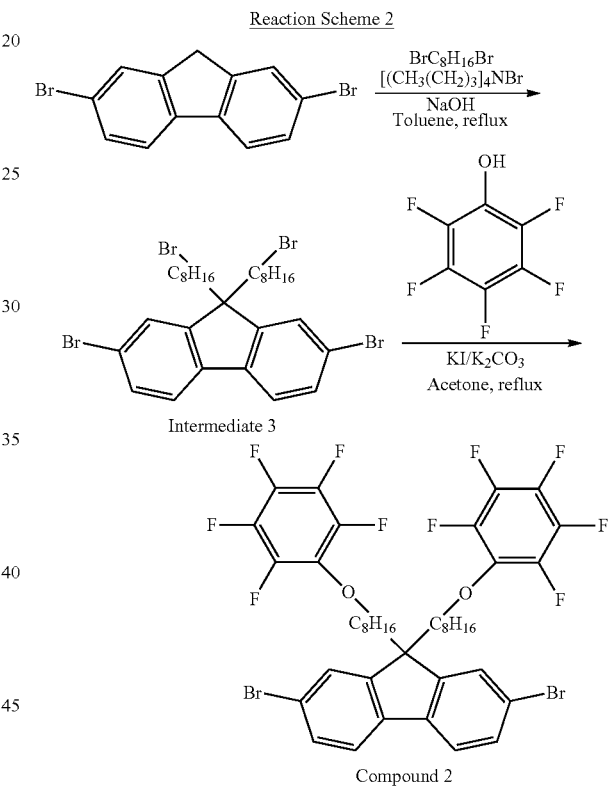

Reaction Scheme 2

Compound 2

(1) Synthesis of Intermediate 3

1 g of 2,7-dibromofluorene, 5 g of 1,8-dibromooctane, and 0.05 g of tetrabutylammonium bromide were mixed with 10 g of a 50% sodium hydroxide solution, and the mixture was maintained at 80° C. After 2 hours, the mixture was cooled to room temperature and the organic layer thereof was subjected to extraction using EA. The solvent was removed under reduced pressure, and the resultant was purified using column chromatography (hexane) to obtain 1.1 g of Intermediate 3 (yield: 50%), and the structure of the product was identified using —NMR.

(2) Synthesis of Compound 2

5 g of 2,7-dibromo-9,9-bis-(8-bromo-octyl)-9H-fluorene, as Intermediate 3, 2.9 g of pentafluorophenol (2.2 equivalents), potassium iodide (0.08 equivalents based on Intermediate 3), and potassium carbonate (5 equivalents based on Intermediate 3) were mixed. After the reaction was terminated, the resultant was purified using column chromatography (hexane) to obtain 5 g of Compound 2 (yield: 77%), and the structure of the product was identified using $^1$H-NMR.

$^1$H-NMR (300 MHz, CDCl$_3$): δ 1.29 (m, 16H), δ 1.43 (m, 4H), δ1.71 (m, 4H), δ1.87 (m, 4H), δ3.94 (t, 4H), δ7.5~7.7 (m, 6H)

Synthesis Example 3

Synthesis of Polymer 1

(1) Synthesis of Monomer A

Monomer A was synthesized through Reaction Scheme 3 below:

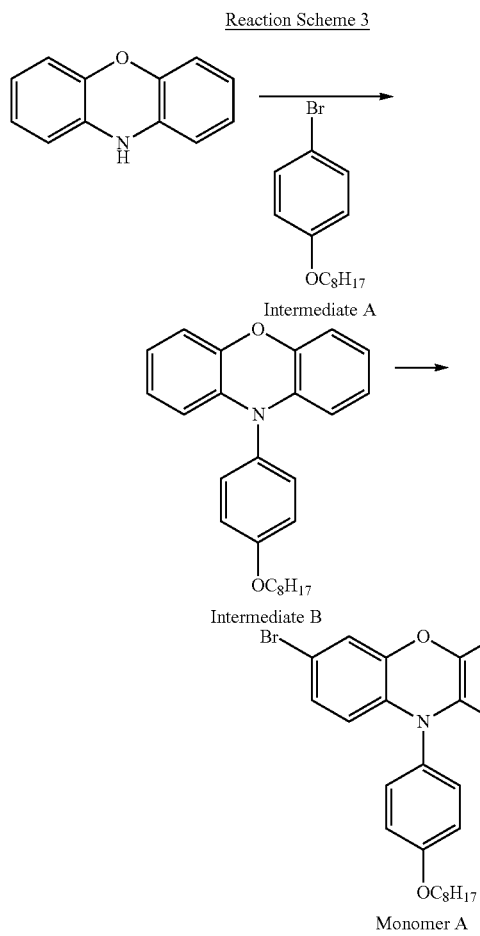

Reaction Scheme 3

Intermediate A

Intermediate B

Monomer A

Synthesis of Intermediate A 50 g of 4-bromophenol (0.29 mol) was dissolved in 500 mL of acetone, and 48.4 g of K$_2$CO$_3$ (0.35 mol) was added thereto. Then, 73.3 g of 1-bromooctane (0.38 mol) was added thereto, and the mixture was refluxed for 24 hours.

After the reaction was terminated, the resultant was subjected to extraction using a solution including water and CHCl$_3$ (water:CHCl$_3$=2:1, v/v) to remove K$_2$CO$_3$. An organic layer was dried using MgSO$_4$ and concentrated, and then silica gel column chromatography was performed using hexane as an eluting solution. The eluate was subjected to distillation under reduced pressure to remove unreacted 1-bromooctane to obtain 80 g of Intermediate A (yield: 96%). The structure of Intermediate A was confirmed using $^1$H-NMR.

Synthesis of Intermediate B 18 g of Intermediate A (64 mmol), 10 g of phenoxazine (54 mmol), 7.4 g of sodium tert-butoxide (77 mmol), 0.61 g of tris(dibenzylidene acetone) dipalladium(0) (Pd(dba)$_2$) (1.1 mmol), and 0.22 g of tri(tert-butyl)phosphine (1.1 mmol) were dissolved in 250 mL of xylene, and the mixture was maintained at 80° C. for 12 hours.

After the reaction was terminated, the mixture was cooled to room temperature, and 200 ml of distilled water was added thereto to perform quenching. Then, the resultant was subjected to extraction using a solution of xylene and water (xylene:water=1:1, v/v). A collected organic layer was dried using MgSO$_4$ and concentrated, and then silica gel column chromatography was performed using a solution of toluene and hexane (toluene:hexane=1:2, v/v) as an eluting solution. The eluate was concentrated and dried to obtain 18.5 g of Intermediate B (yield: 88%). The structure of Intermediate B was confirmed using $^1$H-NMR.

Synthesis of Monomer A 5 g of Intermediate B (13 mmol) was dissolved in 150 mL of CHCl$_3$, and 2.1 equivalents of bromine based on Intermediate B was gradually added thereto while the solution was maintained at 0° C. When the starting material was not observed based on the results of thin layer chromatography (TLC), the addition of bromine to the mixture was stopped, the mixture was stirred for 10 minutes and the reaction was terminated.

A small amount of acetone was added to the mixture for quenching bromine, and the resultant was subjected to extraction using a solution including water and CHCl$_3$ (water:CHCl$_3$=2:1, v/v). A collected organic layer was dried using MgSO$_4$ and concentrated, and then re-precipitated in methanol ("MeOH") to obtain 6 g of Monomer A (yield: 85%). The structure of Monomer A was identified using $^1$H-NMR.

$^1$H-NMR (300 MHz, CDCl$_3$): δ 0.91 (m, 6H), δ1.45 (m, 8H), δ1.82 (m, 1H), δ3.89 (d, 2H), δ5.82 (d, 2H), δ6.5~7.5 (m, 8H)

(2) Synthesis of Polymer 1

0.456 g of Compound 1 (0.5 mmol), 0.273 g of Monomer A (0.5 mmol), 312 mg of bipyridine, 660 mg of Ni(COD)$_2$ (COD=1,5-cyclooctadiene), and 20 mL of tetrahydrofuran ("THF") were added to a 100 mL 2-neck round flask, and the flask was stirred at 60° C. for 24 hours. After the reaction was terminated, the reaction solution was immersed in methanol, and the resultant was filtered and dried to obtain a solid. The solid was dissolved in toluene, and silica gel/alumina column chromatography was performed. The resultant was immersed in methanol again, and filtered and dried to obtain 0.42 g of Polymer 1. As a result of analyzing Polymer 1 using gel permeation chromatography ("GPC"), a number average molecular weight based on polystyrene was 35000 and PDI was 2.51.

Polymer 1

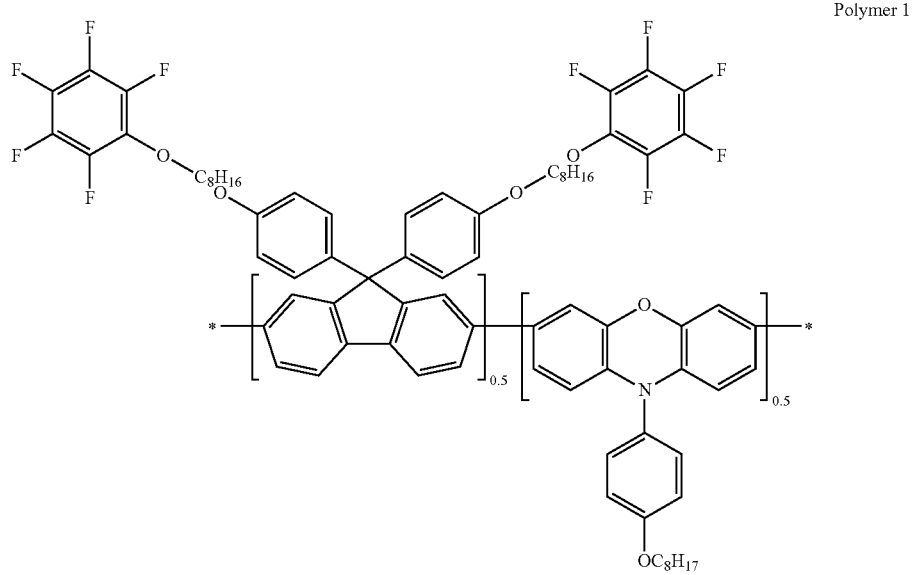

Comparative Example A

Synthesis of Polymer A (1) Synthesis of Compound A

Compound A was synthesized in the same manner as in Synthesis Example 1-(2), except that n-bromooctane was used instead of Intermediate 1. The structure of the product was confirmed using $^1$H-NMR.

$^1$H-NMR (300 MHz, CDCl$_3$): δ 0.89 (t, 6H), δ 1.25~1.50 (m, 12H), δ1.71~1.80 (m, 4H), δ3.90 (t, 4H), 6.76 (d, 4H), δ7.04 (d, 4H), δ7.45~7.6 (m, 6H)

Compound A

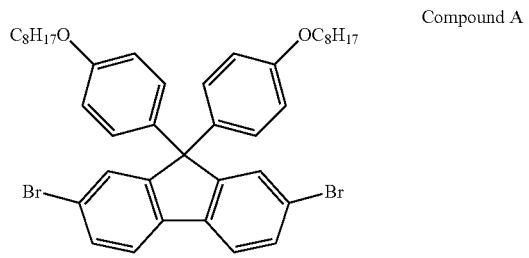

(2) Synthesis of Polymer A

Polymer A was synthesized in the same manner as in Synthesis Example 3-(2), except that Compound A was used instead of Compound 1. Based on GPC analysis of Polymer A, the number average molecular weight based on polystyrene was 24000 and PDI was 2.23.

Polymer A

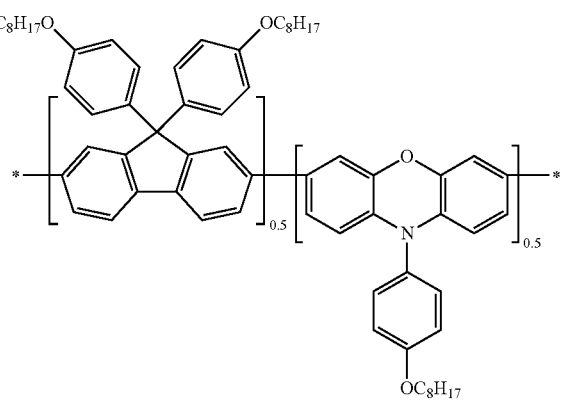

Reference Synthesis Example

Synthesis of EML Forming Material (Polymer 2)

(1) Synthesis of Monomer B

Monomer B was synthesized through Reaction Scheme 4 below:

Reaction Scheme 4

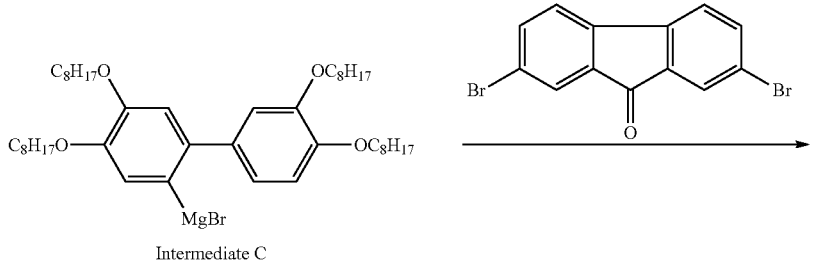

Intermediate C

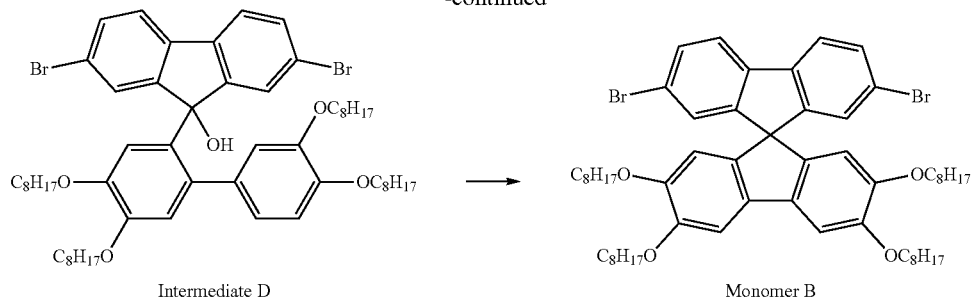

Intermediate D → Monomer B

Synthesis of Intermediate D

A mixture of 50 ml of ether and 8.45 g of Intermediate C (11 mmol) was added to a mixture of 3.36 g of 2,7-dibromo-9-fluorenone (10 mmol) and 50 ml of ether, and the mixture was refluxed overnight. The mixture was cooled, and yellow solid powder was filtered and washed three times with ether. Then, the resultant was added to ammonium chloride, and the mixture was stirred for 10 hours. The precipitate was filtered and washed three times with water. The product was recrystallized using ethanol to obtain yellow solid Intermediate D (yield: 83%).

Preparation of Monomer B 5.0 g of Intermediate D (5 mmol) was added to 15 ml of $CH_3COOH$, and the mixture was subjected to a mild reflux. Then, 0.5 ml of hydrochloric acid was added to the reaction solution, and the resultant was refluxed for 1 hour. After the reaction was terminated, the mixture was cooled to room temperature. Solid powder was filtered and washed three times with water. The product was recrystallized using ethanol to obtain 1.42 g of white powered Monomer B (1.44 mmol, yield: 29%). The structure of Monomer B was confirmed using $^1$H-NMR.

$^1$H-NMR (300 MHz, $CDCl_3$): δ7.60 (d, 2H), δ7.43 (dd, 2H), δ7.16 (d, 2H), δ6.79 (s, 2H), δ6.20 (s, 2H), δ4.18 (m, 4H), δ3.75 (m, 4H), δ1.94 (m, 8H), δ1.72 (m, 8H), δ1.30 (m, 32H), δ0.96 (m, 12H)

(2) Synthesis of EML-Forming Material (Polymer 2)

A Schlenk flask was evacuated and nitrogen-refluxed several times to completely remove moisture. 880 mg of $Ni(COD)_2$ (3.2 mmol) and 500 mg of bipyridyl (3.2 mmol) were added to a glove box, and then the flask was evacuated and nitrogen-refluxed several times. 10 ml of anhydrous dimethylformamide ("DMF"), 346 mg of COD (3.2 mmol), and 10 ml of anhydrous toluene were added to the reaction mixture under a nitrogen atmosphere. The reaction mixture was stirred at 80° C. for 30 minutes, and then 87 mg of Monomer A (0.16 mmol) and 1.42 g (1.44 mmol) of Monomer B which were diluted in 10 ml of toluene were added thereto. Then, 10 ml of toluene was added to thereto while washing the wall of the flask, and then the mixture was stirred at 80□ for 4 days. After 4 days, 1 ml of bromopentafluorobenzene was added thereto, and then the mixture was stirred for one day at 80° C.

After the reaction was completed, the reaction mixture was cooled to 60° C., and a solution including HCl, acetone, and methanol (HCl:acetone:methanol=1:1:2, v/v) was added thereto to form precipitate. The precipitate was dissolved in chloroform, and precipitated in methanol. The resultant was processed using a soxhlet extractor to obtain 620 mg of Polymer 2 (yield: 80%). Based on GPC analysis of Polymer 2, the weight average molecular weight based on polystyrene was 198,000 and PDI was 2.07.

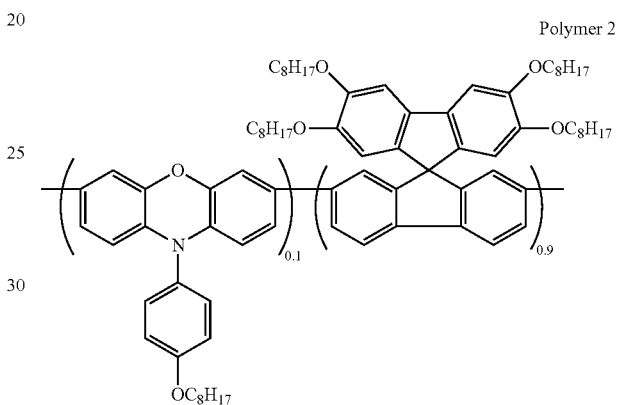

Polymer 2

Example 1

A transparent electrode substrate coated with indium-tin oxide ("ITO") was cleaned. The ITO layer was patterned with a photosensitive resin and an etchant to obtain a desired pattern, and then cleaned. PEDOT (Batron P 4083 manufactured by Bayer) was coated on the ITO layer to a thickness of about 500° C., and then baked at 200□ for about 0.5 hours to form a HIL. A HTL forming composition including 99.2 parts by weight of chlorobenzene and 0.8 parts by weight of Polymer 1 was spin coated on the HIL, and the coating was baked at 180□ for 30 minutes to form a HTL including Polymer 1. An EML forming composition including 99.0 parts by weight of toluene and 1 part by weight of Polymer 2 was spin coated on the HTL, and the coating was baked at 150□ for 30 minutes to form an EML. In this regard, the HTL forming composition and the EML forming composition were filtered using a 0.2 mm filter before spin coated. The thicknesses of the HTL and the EML were respectively 20 nm and 80 nm by controlling the concentration of the compositions and the spin coating rate. Then, $BaF_2$, Ca, and Al were sequentially deposited on the EML while maintaining the degree of vacuum at $4 \times 10^{-6}$ torr or less using a vacuum evaporator to form the EIL and the second electrode. During the vacuum deposition, the thickness of the layer and the growth rate of the layer were controlled using a crystal sensor.

Comparative Example 1

An organic light emitting device was manufactured in the same manner as in Example 1, except that Polymer A was used instead of Polymer 1.

Evaluation Example

Figure 2:
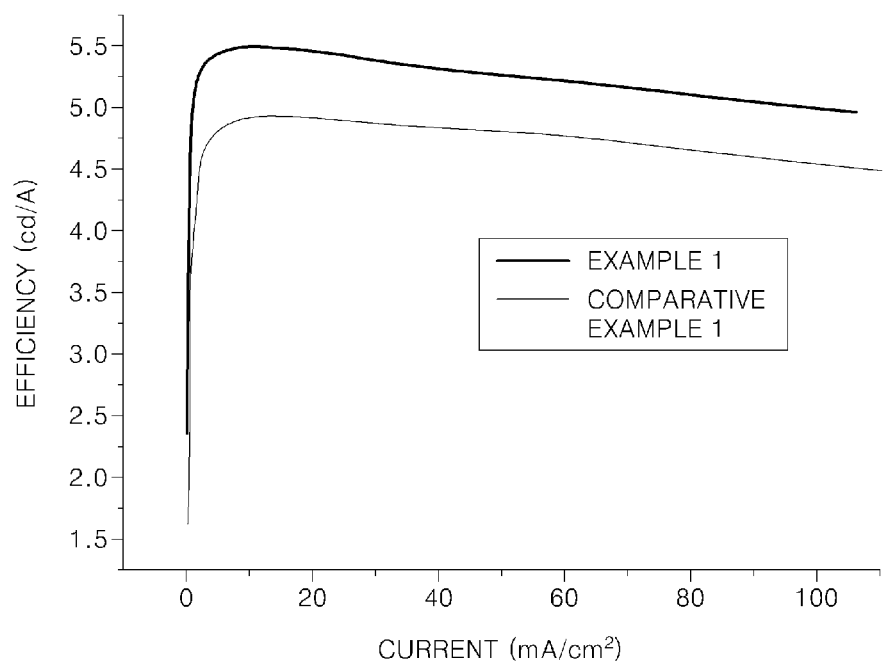
FIG. 2 is a graph illustrating efficiency (cd/A) versus current density (mA/cm$^2$) of organic light emitting devices manufactured according to Example 1 and Comparative Example 1.
Figure 3:
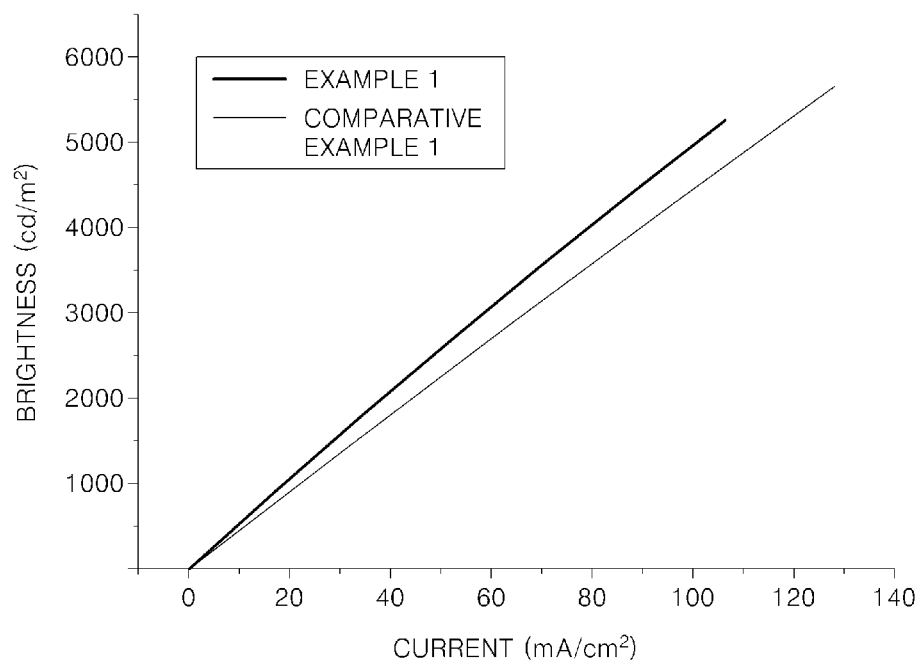
FIG. 3 is a graph illustrating brightness (cd/m$^2$) versus current density (mA/cm$^2$) of organic light emitting devices manufactured according to Example 1 and Comparative Example 1.

Current density-efficiency and current density-brightness characteristics of the organic light emitting devices manufactured according to Example 1 and Comparative Example 1 were evaluated using PR650 Spectroscan Source Measurement Unit. (PhotoReaserch), and the results are shown in FIGS. 2 and 3. Referring to FIGS. 2 and 3, it was identified that the organic light emitting device manufactured according to Example 1 had higher efficiency and brightness than the organic light emitting device manufactured according to Comparative Example 1 at the same current.

As described above, according to the one or more of the above embodiments of the present invention, the organic light emitting device including the fluoro group-containing polymer has excellent electrical characteristics and may be simply manufactured based on a wet process.

It should be understood that the exemplary embodiments described herein should be considered in a descriptive sense only and not for purposes of limitation. Descriptions of features or aspects within each embodiment should typically be considered as available for other similar features or aspects in other embodiments. It should be understood that this disclosure is not limited to the disclosed embodiments, but, on the contrary, is intended to cover various modifications and equivalent arrangements included within the spirit and scope of the appended claims.

What is claimed is:

1. A fluoro group-containing polymer represented by Formula 11 below:

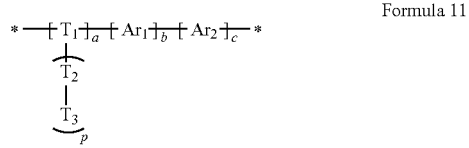

Formula 11 wherein $T_1$ is a substituted or unsubstituted $C_6$-$C_{30}$ aromatic ring;

$T_2$ is a bivalent linking group represented by —[C($R_1$)($R_2$)]$_q$—, wherein $R_1$ and $R_2$ are a hydrogen atom, q is 10, and i) one of —C($R_1$)($R_2$)— is replaced —O— or a substituted or unsubstituted $C_6$-$C_{30}$ arylene group; two of —C($R_1$)($R_2$)— are each independently replaced —O— or a substituted or unsubstituted $C_6$-$C_{30}$ arylene group; or iii) three of —C($R_1$)($R_2$)— are each independently replaced —O— or a substituted or unsubstituted $C_6$-$C_{30}$ arylene group;

$T_3$ is represented by —($R_3$)$_r$—$R_4$, wherein $R_3$ is selected from a fluoro group-containing $C_6$-$C_{30}$ arylene group, $R_4$ is selected from a halogen atom, and r is 1, wherein the $R_3$s may be same or different from each other;

p is 2;

$Ar_1$ and $Ar_2$ are each independently selected from a substituted or unsubstituted $C_3$-$C_{30}$ heteroarylene group;

a, b, and c are each independently a real number satisfying $0<a\leq0.99$, $0<b\leq0.99$, and c−0, and a+b+c−1; and each "*" indicates a point of attachment to the same or a different polymeric unit represented by Formula 11.

2. The fluoro group-containing polymer of claim 1, wherein $T_1$ is an anthracene ring, a fluorene ring, a pyrene ring, or a chrysene ring.

3. The fluoro group-containing polymer of claim 1, wherein $T_2$ is represented by Formula 2A or 2B below:

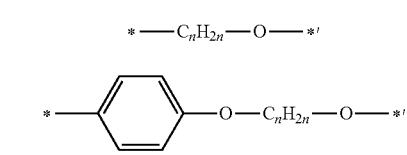

wherein * is a binding site to $T_1$ of Formula 1, *' is a binding site to $T_3$ of Formula 1, and n in Formula 2A is 9 and n in Formula 2B is 7.

4. The fluoro group-containing polymer of claim 1, wherein $R_3$ is a fluoro group-containing phenylene group, a fluoro group-containing naphthylene group, or a fluoro group-containing anthrylene group.

5. The fluoro group-containing polymer or claim 1, wherein the fluorination degree of $T_3$ ranges from 50% to 100%.

6. The fluoro group-containing polymer of claim 1, wherein $Ar_1$ and $Ar_2$ are each independently substituted or unsubstituted pyrrolylene, substituted or unsubstituted imidazolylene, substituted or unsubstituted pyrazolylene, substituted or unsubstituted pyridinylene, substituted or unsubstituted pyrazinylene, substituted or unsubstituted pyrimidinylene, substituted or unsubstituted pyridazinylene, substituted or unsubstituted isoindolylene, substituted or unsubstituted indolylene, substituted or unsubstituted indazolylene, substituted or unsubstituted purinylene, substituted or unsubstituted quinolinylene, substituted or unsubstituted benzoquinolinylene, substituted or unsubstituted phthalazinylene, substituted or unsubstituted naphthyridinylene, substituted or unsubstituted quinoxalinylene, substituted or unsubstituted quinazolinylene, substituted or unsubstituted cinnolinylene, substituted or unsubstituted carbazolylene, substituted or unsubstituted phenanthridinylene, substituted or unsubstituted acridinylene, substituted or unsubstituted phenanthrolinylene, substituted or unsubstituted phenazinylene, substituted or unsubstituted benzothiazolylene, substituted or unsubstituted benzooxazolylene, substituted or unsubstituted benzoimidazolylene, substituted or unsubstituted puranylene, substituted or unsubstituted benzopuranylene, substituted or unsubstituted thiophenylene, substituted or unsubstituted benzothiophenylene, substituted or unsubstituted thiazolylene, substituted or unsubstituted isothiazolylene, substituted or unsubstituted isoxazolylene, substituted or unsubstituted oxazolylene, substituted or unsubstituted benzo-oxazolylene, or any one of groups represented by Formulae 12A to 12E and 12G:

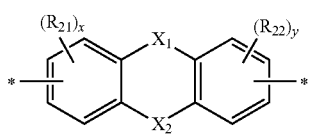

Formula 12A

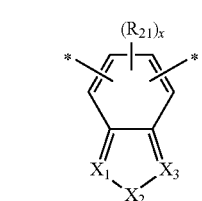

Formula 12B

-continued

Formula 12C
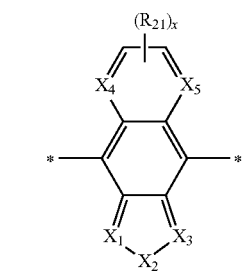

Formula 13A
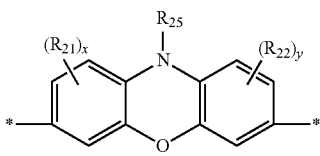

Formula 13B
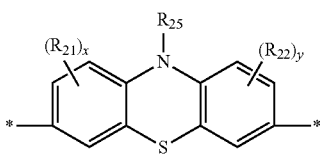

Formula 12D
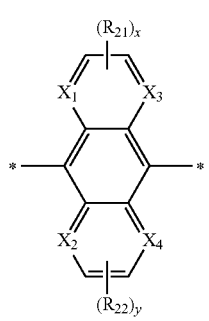

Formula 13C
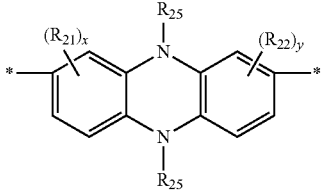

Formula 12E
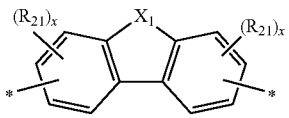

Formula 13D
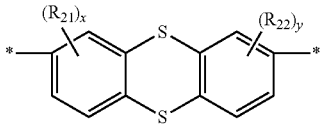

Formula 12G
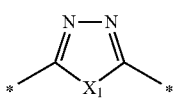

Formula 13E
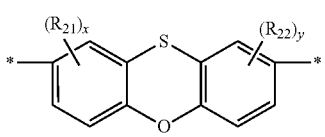

wherein $X_1$ to $X_5$ are each independently selected from O, S, C(=O), N($R_{25}$), and C($R_{25}$)($R_{26}$); $R_{21}$, $R_{22}$, $R_{25}$ and $R_{26}$ are each independently a hydrogen atom, a substituted or unsubstituted $C_1$-$C_{30}$ alkyl group, a substituted or unsubstituted $C_1$-$C_{30}$ alkoxy group, or a substituted or unsubstituted aryl group; and x and y are each independently an integer ranging from 1 to 4;

wherein at least one of $X_1$ and $X_2$ in Formula 12A is O, S or N($R_{25}$), at least one of $X_1$ to $X_3$ in Formula 12B is O, S or N($R_{25}$), at least one of $X_1$ to $X_5$ in Formula 12C is O, S or N($R_{25}$), at least one of $X_1$ and $X_4$ in Formula 12 is O, S or N($R_{25}$)

$X_1$ in Formula 12E is O, S or N($R_{25}$), and each "*" indicates a point of attachment to $T_1$, $Ar_1$ or $Ar_2$ in Formula 11.

7. The fluoro group-containing polymer of claim 1, wherein $Ar_1$ and $Ar_2$ are each independently any one of groups represented by Formulae 13A through 13K and 13M below Formula 13F
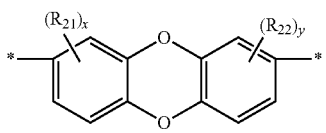

Formula 13G
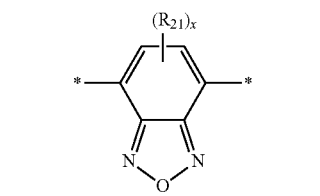

-continued

Formula 13H
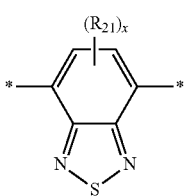

Formula 13I
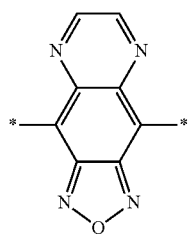

Formula 13J
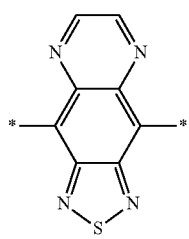

Formula 13K
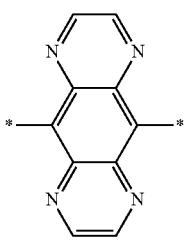

Formula 13M
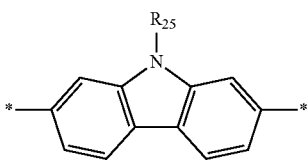

wherein $R_{21}$, $R_{22}$, and $R_{25}$ are each independently a hydrogen atom; a $C_1$-$C_{10}$ alkyl group; a $C_1$-$C_{10}$ alkoxy group; a $C_6$-$C_{14}$ aryl group; or a $C_6$-$C_{14}$ aryl group substituted with at least one $C_1$-$C_{30}$ alkyl group, $C_1$-$C_{30}$ alkoxy group, $C_2$-$C_{30}$ alkenyl group, or $C_6$-$C_{30}$ aryl group; x is an integer ranging from 1 to 4; $R_{11}$ is a $C_1$-$C_{10}$ alkyl group or a $C_6$-$C_{14}$ aryl group; and each "*" indicates a point of attachment to $T_1$, $Ar_1$ or $Ar_2$ in Formula 11.

8. The fluoro group-containing polymer of claim 1, wherein $Ar_1$ is represented by Formula 14A below:

Formula 14A
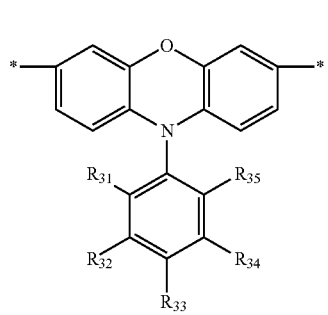

wherein $R_{31}$ to $R_{35}$ are each independently a hydrogen atom, a $C_1$-$C_{30}$ alkyl group, a $C_1$-$C_{30}$ alkoxy group, a $C_2$-$C_{30}$ alkenyl group, or a $C_6$-$C_{30}$ aryl group and each "*" indicates a point of attachment to $T_1$ or $Ar_2$ in Formula 11.

9. A fluoro group-containing polymer of claim 1, wherein the polymer is represented by Formula 11A below:

Formula 11A
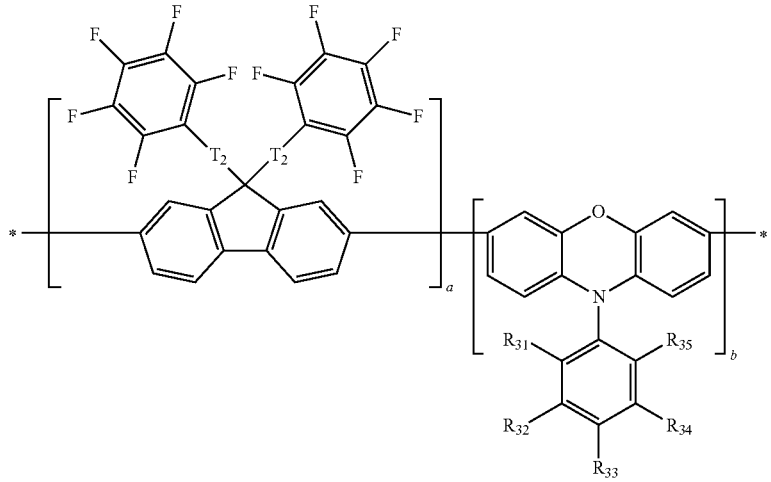

wherein in Formula 11A, $T_2$ is represented by Formula 2A or 2B;

$R_{31}$ to $R_{35}$ are each independently a hydrogen atom, a $C_1$-$C_{30}$ alkyl group, a $C_1$-$C_{30}$ alkoxy group, a $C_2$-$C_{30}$ alkenyl group, or a $C_6$-$C_{30}$ aryl group;

a and b are each independently a real number satisfying 0<a≤0.99 and 0<b≤0.99, and a+b−1; and each "*" indicates a point of attachment to the same or a different polymeric unit represented by Formula 11A:

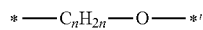

Formula 2A

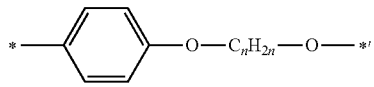

Formula 2B

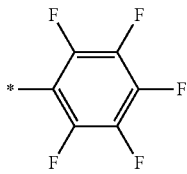

Formula 3A wherein * in Formulae 2A and 2B is a binding site to a fluorene of Formula 11A, *' in Formulae 2A and 2B is a binding site to Formula 3A in Formula 11A and * in Formula 3A is a binding site to $T_2$ of Formula 11A and n in Formula 2A is 9 and n in Formula 2B is 7.

10. An organic light emitting device comprising:
a substrate; a first electrode; a second electrode; an intermediate layer that is interposed between the first electrode and the second electrode and comprising a fluoro group-containing polymer according to claim 1; and an emission layer (EML) that is formed close to the intermediate layer.

11. The organic light emitting device of claim 10, wherein the EML comprises a polymer represented by Formula 21 below:

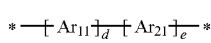

Formula 21 wherein $Ar_{11}$ and $Ar_{12}$ are each independently a substituted or unsubstituted $C_6$-$C_{30}$ arylene group; a substituted or unsubstituted $C_3$-$C_{30}$ heteroarylene group; or a system including a substituted or unsubstituted $C_6$-$C_{30}$ arylene group and a substituted or unsubstituted $C_3$-$C_{30}$ heteroarylene group which are connected to each other by a single bond or by a linking group represented by —N($R_{51}$)—, wherein $R_{51}$ is a hydrogen atom, a substituted err unsubstituted $C_1$-$C_{30}$ alkyl group, or a substituted or unsubstituted $C_6$-$C_{30}$ aryl group;

d and e are each independently a real number satisfying 0<d≤0.99 and 0<e≤0.99, and d+e=1; and each "*" indicates a point of attachment to the same or a different polymeric unit represented by Formula 21.

12. A method of manufacturing an organic light emitting device, the method comprising:
forming a first electrode on a substrate;
forming an intermediate layer comprising a fluoro group-containing polymer according to claim 1 by applying a first composition for forming an intermediate layer including the fluoro group-containing polymer according to claim 1 and a first solvent to the first electrode, and baking the first composition at a temperature for a time period suitable for removing the first solvent;
forming an emission layer by applying a second composition for forming an emission layer including an emission layer-forming material and a second solvent to the intermediate layer, and heat-treating the second composition; and
forming a second electrode on the emission layer.

* * * * *